(12) United States Patent
Powell

(10) Patent No.: US 11,274,302 B2
(45) Date of Patent: *Mar. 15, 2022

(54) SPECIFIC SYNTHETIC CHIMERIC XENONUCLEIC ACID GUIDE RNA; S(XNA-GRNA) FOR ENHANCING CRISPR MEDIATED GENOME EDITING EFFICIENCY

(71) Applicant: Michael J Powell, Alamo, CA (US)

(72) Inventor: Michael J Powell, Alamo, CA (US)

(73) Assignee: DIACARTA LTD, George Town (KY)

( * ) Notice: Subject to any disclaimer, the term of this patent is extended or adjusted under 35 U.S.C. 154(b) by 904 days.

This patent is subject to a terminal disclaimer.

(21) Appl. No.: 15/786,591

(22) Filed: Oct. 17, 2017

(65) Prior Publication Data

US 2018/0066258 A1 Mar. 8, 2018

Related U.S. Application Data

(60) Provisional application No. 62/376,206, filed on Aug. 17, 2016, provisional application No. 62/376,287, filed on Aug. 17, 2016.

(51) Int. Cl.
*C12N 15/113* (2010.01)
*C12N 15/90* (2006.01)
*C07H 21/00* (2006.01)

(52) U.S. Cl.
CPC .......... *C12N 15/113* (2013.01); *C12N 15/907* (2013.01); *C07H 21/00* (2013.01); *C12N 2310/20* (2017.05); *C12N 2310/3517* (2013.01); *C12N 2310/3519* (2013.01)

(58) Field of Classification Search
None
See application file for complete search history.

(56) References Cited

U.S. PATENT DOCUMENTS

2014/0068797 A1* 3/2014 Doudna ............... A61K 38/465
800/18

OTHER PUBLICATIONS

Ustinov et al. Russian Journal of Bioorganic Chemistry 2010, 36(4)401-445 (Year: 2010).*
Xiong et al., Annu. Rev. Genom. Hum. Genet. 2016. 17:131-54.*

* cited by examiner

*Primary Examiner* — James D Schultz
(74) *Attorney, Agent, or Firm* — Isaac Angres

(57) ABSTRACT

The invention provides specific synthetic chimeric xenonucleic acid guide RNA; s(XNA-gRNA) for enhancing crispr mediated genome editing efficiency. The invention also provides methods and compositions for inducing CRISPR/Cas-based gene editing/regulation (e.g., genome editing or gene expression) of a target nucleic acid (e.g., target DNA or target RNA) in a cell. The methods include using single guide RNAs (sgRNAs) that have been chemically modified with xeno nucleic acids which enhance gene regulation of the target nucleic acid in a primary cell for use in ex vivo therapy or in a cell in a subject for use in in vivo therapy. Additionally, provided herein are methods for preventing or treating a genetic disease in a subject by administering a sufficient amount of a sgRNA that has been chemically modified with xeno nucleic acids to correct a mutation in a target gene associated with the genetic disease.

7 Claims, 5 Drawing Sheets

Specification includes a Sequence Listing.

Figure 2

CRISPR gRNA: SEQ ID NO: 1  5'-gUGGACUCAUGAUCACGGGUCGUUUAGAGCUA-3' tracrRNA: SEQ ID NO: 2  5'-AGCAAGUUAAAAUAAGGCUAGUCCGUUAUCAACUUG
AAAAGUGGCACCGAGUC GGUGC-3'

TET Repressor EGFP /CRISPR/Cas9 Target Site: SEQ ID NO: 3

PAM  I Cut Site

AGATCTACCATGCCAAAGAGACCCAGACCCCGTGATCATGAGTCCAAAGAGAAGAACACA
GGCAGAGCGGCAATGGAGACCCAG

SEQ ID NO: 4

TCTAGATGGTACGGTTCTCTGGGTCTGGGCACTAGTACTCAGGTTTCTCTTCTTGTCC
GTCTCGGCGTTACCCTCTGGGTC gRNA

SPECIFIC SYNTHETIC CHIMERIC XENONUCLEIC ACID GUIDE RNA; S(XNA-GRNA) FOR ENHANCING CRISPR MEDIATED GENOME EDITING EFFICIENCY

This application claims the priority benefit under 35 U.S.C. section 119 of U.S. Provisional Patent Application No. 62/376,206 entitled "Specific Synthetic Chimeric Xenonucleic Acid Guide RNA; s(XNA-gRNA) For Enhancing CRISPR Mediated Genome Editing Efficiency" filed on Aug. 17, 2016; and Provisional Patent Application No. 62/376,287 entitled "Synthetic Routes To Xenonucleic Acid (Xna) Monomers" which are in their entirety herein incorporated by reference.

FIELD OF THE INVENTION

The present invention relates to the field of molecular biology. In particular, the present invention relates to the clusters of regularly interspaced short palindromic repeats (CRISPR) technology. This invention also pertains to modified compositions for use in CRISPR systems, and their methods of use.

The invention further relates to CRISPR-related methods and components for editing of, or delivery of a payload to, a target nucleic acid sequence. The present disclosure also generally relates to compositions and methods for the genetic modification of cells. In particular, the disclosure relates to CRISPR reagents and the use of such reagents.

BACKGROUND OF THE INVENTION

Genome engineering can refer to altering the genome by inserting, deleting, mutating, or substituting specific nucleic acid sequences. The altering can be gene or location specific. Genome engineering can use nucleases to cut a nucleic acid thereby generating a site for the alteration. Engineering of non-genomic nucleic acid is also contemplated. A protein containing a nuclease domain can bind and cleave a target nucleic acid by forming a complex with a nucleic acid-targeting nucleic acid. In one example, the cleavage can introduce double stranded breaks in the target nucleic acid. A nucleic acid can be repaired e.g. by endogenous non-homologous end joining (NHEJ) machinery. In a further example, a piece of nucleic acid can be inserted. Modifications of nucleic acid-targeting nucleic acids and site-directed polypeptides can introduce new functions to be used for genome engineering.

After the human genome project, the sequence of every gene in the human genome is now known. However, the function of most genes is still not clear. One of the most common strategies for studying the function of a particular gene is to knock it out in a model organism. However, until recently, gene knockout could only be done in certain animals, and the cost has been very high. The CRISPR-Cas9 system has now emerged as a powerful genome-editing technology that can knock out any gene in cultured cells with ease.

The use of clustered regularly interspaced short palindromic repeats (CRISPR) and associated Cas proteins (CRISPR-Cas system) for site-specific DNA cleavage has shown great potential for a number of biological applications.

This powerful and revolutionary technology has already become one of the most commonly used tools in biological research. Almost all of the major companies, including Life Technologies, Sigma, and Santa Cruz Biotechnology, provide services based on this technology. Moreover, CRISPR-Cas9 technology has been actively pursued as a therapeutic tool for treating various diseases. A CRISPR-Cas9 system with increased knockout efficiency will be of great interest. The current commonly used single-guide RNA (sgRNA) has a shortened duplex structure compared with the native bacterial crRNA-tracrRNA duplex.

CRISPR (Clustered Regularly Interspaced Short Palindromic Repeats) is a method of gene editing that utilizes the Cas9 protein and specific guide RNAs to either disrupt host genes or insert sequences of interest. Initially used in bacteria as an adaptive immunity response, CRISPR has been since utilized in the biological field as a new alternative to genome engineering. Furthermore, CRISPR provides a cheaper alternative to other gene editing techniques such as zinc fingers, and is quickly being adopted as the technique of choice.

Cas9 (CRISPR associated protein 9) is a naturally occurring enzyme found in some bacteria that is used for immunity. Cas9 works by using guide RNA with short sequences complimentary to potential foreign DNA, combating infection. This mechanism has similarities to RNA interference found in many eukaryotes. Because of its capabilities, Cas9 has been used recently in experiments to serve as a genome editing tool.

CRISPR/Cas9 systems are a versatile tool for genome editing due to the highly efficient targeting of DNA sequences complementary to their RNA guide strands. However, it has been shown that RNA guided Cas9 nuclease cleaves genomic DNA sequences containing mismatches to the guide strand. The use of chemically modified and protected nucleoside phosphoramidites for the synthesis of single guide RNAs (sgRNAs) to enhance genome editing efficiency in human primary T cells, CD34+ hematopoietic stem and progenitor cells has been reported. The researchers argued that co-delivery of chemically modified sgRNAs with Cas9 mRNA or protein is an efficient RNA- or ribonucleoprotein (RNP)-based delivery method for the CRISPR-Cas system. This approach is a simple and effective way for the development of new genome editing methods.

Additionally, genome editing with engineered nucleases is a breakthrough technology for modifying essentially any genomic sequence of interest. This technology exploits engineered nucleases to generate site-specific double-strand breaks (DSBs) followed by resolution of DSBs by endogenous cellular repair mechanisms. The outcome can be either mutation of a specific site through mutagenic nonhomologous end-joining (NHEJ), creating insertions or deletions (in/dels) at the site of the break, or precise change of a genomic sequence through homologous recombination (HR) using an exogenously introduced donor template. A recent major addition to this platform is the clustered regularly interspaced palindromic repeat (CRISPR)/Cas system consisting of an RNA-guided nuclease (Cas) and a short guide RNA (sgRNA). The guide RNA is composed of two RNAs termed CRISPR RNA (crRNA) and trans-activating crRNA (tracrRNA), which are typically fused in a chimeric single guide RNA (sgRNA). sgRNAs for genome editing can consist of 100 nucleotides (nt) of which 20 nt at the 5' end hybridize to a target DNA sequence by means of Watson-Crick base pairing and guide the Cas endonuclease to cleave the target genomic DNA.

The native prokaryotic CRISPR-Cas system comprises an array of short repeats with intervening variable sequences of constant length (i.e., clusters of regularly interspaced short palindromic repeats, or "CRISPR"), and CRISPR-associated ("Cas") proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a Cas nuclease. The gRNA:Cas nuclease complex binds a target polynucleotide sequence having a protospacer adjacent motif ("PAM") and a protospacer, which is a sequence complementary to a portion of the gRNA. The recognition and binding of the target polynucleotide by the gRNA:Cas nuclease complex induces cleavage of the target polynucleotide. The native CRISPR-Cas system functions as an immune system in prokaryotes, where gRNA:Cas nuclease complexes recognize and silence exogenous genetic elements in a manner analogous to RNAi in eukaryotic organisms, thereby conferring resistance to exogenous genetic elements such as plasmids and phages.

It has been demonstrated that a single-guide RNA ("sgRNA") can replace the complex formed between the naturally-existing crRNA and tracrRNA.

Considerations relevant to developing a gRNA, including a sgRNA, include specificity, stability, and functionality. Specificity refers to the ability of a particular gRNA:Cas nuclease complex to bind to and/or cleave a desired target sequence, whereas little or no binding and/or cleavage of polynucleotides different in sequence and/or location from the desired target occurs. Thus, specificity refers to minimizing off-target effects of the gRNA:Cas nuclease complex. Stability refers to the ability of the gRNA to resist degradation by enzymes, such as nucleases, and other substances that exist in intra-cellular and extra-cellular environments. Thus, there is a need for providing gRNA, including sgRNA, having increased resistance to nucleolytic degradation, increased binding affinity for the target polynucleotide, and/or reduced off-target effects while, nonetheless, having gRNA functionality. Further considerations relevant to developing a gRNA include transfectability and immunostimulatory properties. Thus, there is a need for providing gRNA, including sgRNA, having efficient and titratable transfectability into cells, especially into the nuclei of eukaryotic cells, and having minimal or no immunostimulatory properties in the transfected cells. Another important consideration for gRNA is to provide an effective means for delivering it into and maintaining it in the intended cell, tissue, bodily fluid or organism for a duration sufficient to allow the desired gRNA functionality.

The CRISPR/Cas system has also been adapted for sequence-specific control of gene expression, e.g., inhibition or activation of gene expression. Using particular Cas9 polypeptide variants that lack endonuclease activity, target genes can be repressed or activated. Unfortunately, genome editing and modulating gene expression using the CRISPR/Cas system remains inefficient, especially in primary cells. As such, there remains a need in the art for improved compositions and methods based on the CRISPR/Cas system that can be used for gene regulation, e.g., genome editing with enhanced efficiency, inhibiting gene expression, and activating gene expression. The present invention satisfies this need and provides additional advantages as well.

BRIEF DESCRIPTION OF THE FIGURES

FIG. 2 features the sequences used for the gene editing using the xenonucleic acids of the invention.

SUMMARY OF THE INVENTION

The invention provides specific synthetic chimeric xenonucleic acid guide RNA; s(XNA-gRNA) for enhancing crispr mediated genome editing efficiency.

Figure 1:
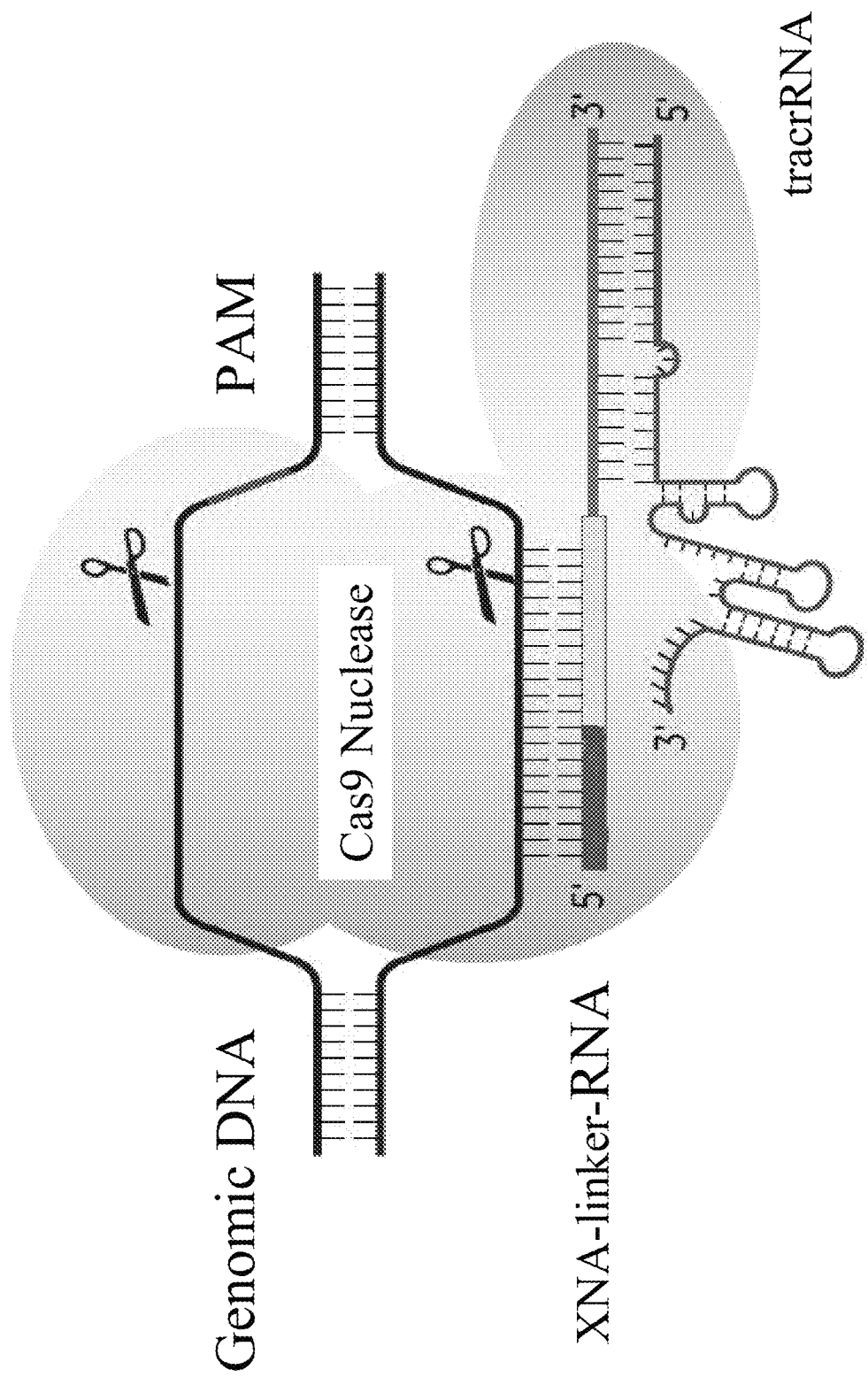
FIG. 1 illustrates the method of the invention using the XNA-RNA Chimera in CRISPR-Cas9 Gene Editing.
Figure 3:
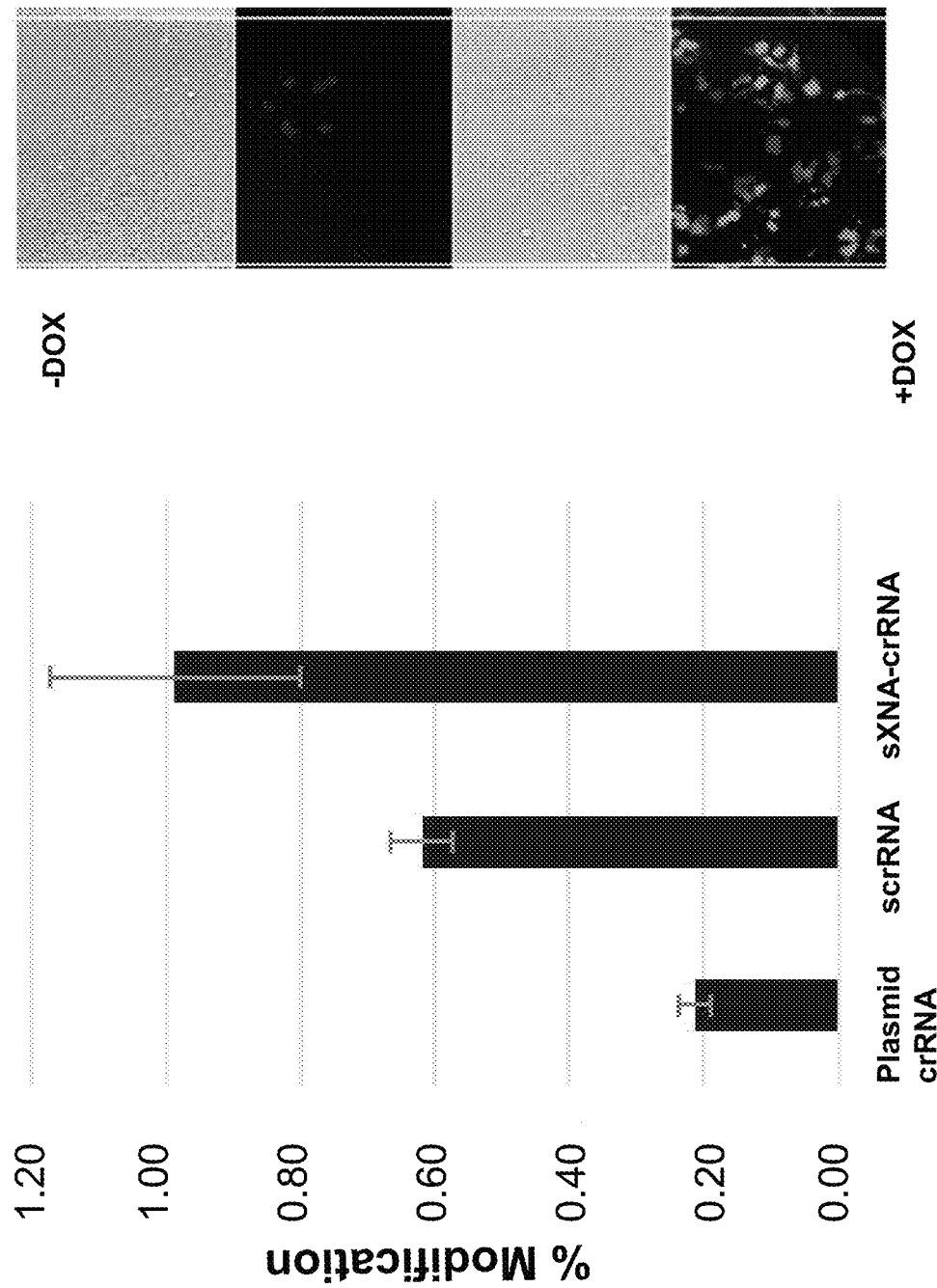
FIG. 3 shows the efficiency of CRISPR mediated gene as measured by EGFP expression in HEK293 cells.

The present invention also provides a more efficient approach that utilizes a chimeric XNA-gRNA construct that can be targeted specifically to cells of interest. Since XNA's have a neutral non-phosphate containing backbone they are totally resistant to nucleases and also bind more avidly to complementary target sequences that the natural RNA analogs. XNA-gRNA chimeras (XNA-linker-RNA in FIG. 1.) can be targeted efficiently to any genetic locus and induce highly efficient CRISPR mediated gene editing at the targeted locus. The gene target site specific XNA-gRNA chimera is used together with a chemically synthesized trans-activating CRISPR RNA (tracrRNA) which complexes with the crRNA to recruit Cas9 nuclease.

The present invention also provides methods for inducing (e.g., initiating, modulating, enhancing, etc.) gene editing/regulation of a target nucleic acid in a cell. The invention includes using xenonucleic acid modified single guide RNAs (sgRNAs) that enhance genome editing and/or inhibition or activation of gene expression of a target nucleic acid in a primary cell (e.g., cultured in vitro for use in ex vivo therapy and other genetic engineering applications such as plant engineering) or in a cell in a subject such as a human (e.g., for use in in vivo therapy). The present invention also provides methods for preventing or treating a disease in a subject by enhancing precise genome editing to correct a mutation in a target gene associated with the disease. The present invention can be used with any cell type and at any gene locus that is amenable to nuclease-mediated genome editing technology.

DETAILED DESCRIPTION OF THE INVENTION

The instant invention is directed to methods for enhancing the efficiency of CRISPR/Cas-based genome editing and/or modulation of gene expression in an in vitro cell (e.g., a primary cell for use in ex vivo therapy) or an in vivo cell (e.g., a cell in an organ or tissue of a subject such as a human). The invention is applicable to any type of cells i.e., cells derived from all mammals as well as other animal species and botanical plants. In particular, the methods provided herein utilize single guide RNAs (sgRNAs) which have been modified with xenonucleic acids and therefore have enhanced activity during gene regulation (e.g., genome editing, inhibition of gene expression, and activation of gene expression) compared to corresponding unmodified sgRNAs. In certain aspects, the present invention provides methods for gene regulation of a target nucleic acid in a cell by introducing a chemically modified sgRNA (i.e., a xenonucleic acid modified sgRNA) that hybridizes to the target nucleic acid together with either a Cas nuclease (e.g., Cas9 polypeptide) or a variant or fragment thereof, an mRNA encoding a Cas nuclease (e.g., Cas9 polypeptide) or a variant or fragment thereof, or a recombinant expression vector comprising a nucleotide sequence encoding a Cas nuclease (e.g., Cas9 polypeptide) or a variant or fragment thereof. In certain other aspects, the present invention provides methods for preventing or treating a genetic disease in a subject by administering a sufficient amount of the xenonucleic acid modified sgRNA to correct a genetic mutation associated with the disease.

The practice of the present invention employs, unless otherwise indicated, conventional techniques of immunology, biochemistry, chemistry, synthetic organic chemistry, molecular biology, microbiology, cell biology, genomics and recombinant DNA, which are within the skill of the art. See Sambrook, Fritsch and Maniatis, Molecular Cloning: A Laboratory Manual, 2nd edition (1989), Current Protocols in Molecular Biology (F. M. Ausubel, et al. eds., (1987)), the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)).

Oligonucleotides that are not commercially available can be chemically synthesized, e.g., according to the solid phase phosphoramidite triester method first described by Beaucage and Caruthers, Tetrahedron Lett. 22: 1859-1862 (1981), using an automated synthesizer, as described in Van Devanter et. al, Nucleic Acids Res. 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, J. Chrom. 255: 137-149 (1983).

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention.

The term "primary cell" refers to a cell isolated directly from a multicellular organism. Primary cells typically have undergone very few population doublings and are therefore more representative of the main functional component of the tissue from which they are derived in comparison to continuous (tumor or artificially immortalized) cell lines.

The term "genome editing" refers to a type of genetic engineering in which DNA is inserted, replaced, or removed from a target DNA, e.g., the genome of a cell, using one or more nucleases and/or nickases. The nucleases create specific double-strand breaks (DSBs) at desired locations in the genome, and harness the cell's endogenous mechanisms to repair the induced break by homology-directed repair (HDR) (e.g., homologous recombination) or by nonhomologous end joining (NHEJ). The nickases create specific single-strand breaks at desired locations in the genome. In one non-limiting example, two nickases can be used to create two single-strand breaks on opposite strands of a target DNA, thereby generating a blunt or a sticky end. Any suitable nuclease can be introduced into a cell to induce genome editing of a target DNA sequence including, but not limited to, CRISPR-associated protein (Cas) nucleases, zinc finger nucleases (ZFNs), transcription activator-like effector nucleases (TALENs), meganucleases, other endo- or exonucleases, variants thereof, fragments thereof, and combinations thereof. In particular embodiments, nuclease-mediated genome editing of a target DNA sequence can be "induced" or "modulated" (e.g., enhanced) using the modified single guide RNAs (sgRNAs) described herein in combination with Cas nucleases (e.g., Cas9 polypeptides or Cas9 mRNA), e.g., to improve the efficiency of precise genome editing via homology-directed repair (HDR).

The term "nucleic acid," "nucleotide," or "polynucleotide" refers to deoxyribonucleic acids (DNA), ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. In some embodiments, a nucleic acid can comprise a mixture of DNA, RNA and analogs thereof. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al, Nucleic Acid Res. 19:5081 (1991); Ohtsuka et al, J. Biol. Chem. 260:2605-2608 (1985); and Rossolini et al, Mol. Cell. Probes 8:91-98 (1994)). The term nucleic acid is used interchangeably with gene, cDNA, and mRNA encoded by a gene.

The term "gene" or "nucleotide sequence encoding a polypeptide" means the segment of DNA involved in producing a polypeptide chain. The DNA segment may include regions preceding and following the coding region (leader and trailer) involved in the transcription/translation of the gene product and the regulation of the transcription/translation, as well as intervening sequences (introns) between individual coding segments (exons). [0045] The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "effective amount" or "sufficient amount" refers to the amount of an agent (e.g., Cas nuclease, modified single guide RNA, etc.) that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other agents, timing of administration, and the physical delivery system in which it is carried. [0058] The term "pharmaceutically acceptable carrier" refers to a substance that aids the administration of an agent (e.g., Cas nuclease, modified single guide RNA, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention. [0059] The term "increasing stability," with respect to components of the CRISPR system, refers to modifications that stabilize the structure of any molecular component of the CRISPR system. The term includes modifications that decrease, inhibit, diminish, or reduce the degradation of any molecular component of the CRISPR system.

The term "enhanced activity," with respect to components of the CRISPR system and in the context of gene regulation, refers to an increase or improvement in the efficiency and/or the frequency of inducing, modulating, regulating, or controlling genome editing and/or gene expression.

The present invention provides methods for inducing gene regulation of a target nucleic acid in a cell. The invention includes using xenonucleic acid modified single guide RNAs (sgRNAs) that enhance genome editing and/or inhibition or activation of gene expression of a target nucleic acid in a primary cell (e.g., cultured in vitro for use in ex vivo therapy) or in a cell in a subject such as a human (e.g., for use in in vivo therapy). The present invention also provides methods for preventing or treating a disease in a subject by enhancing precise genome editing to correct a mutation in a target gene associated with the disease. The present invention can be used with any cell type and at any gene locus that is amenable to nuclease-mediated genome editing technology.

The present invention is also directed to a method for inducing (e.g., initiating, modulating, enhancing, efficient editing, etc.) gene regulation of a target nucleic acid in a primary cell, the method comprising: introducing into the primary cell: (a) a xenonucleic acid modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are nucleotides which have been chemically modified with xenonucleic acids; and (b) a Cas polypeptide, an mRNA encoding a Cas polypeptide, and/or a recombinant expression vector comprising a nucleotide sequence encoding a Cas polypeptide, wherein the xenonucleic acid modified sgRNA guides the Cas polypeptide to the target nucleic acid, and wherein the xenonucleic acid modified sgRNA induces gene regulation of the target nucleic acid with an enhanced activity and efficiency relative to a corresponding unmodified sgRNA.

The enhanced activity and efficiency comprises increased stability of the xenonucleic acid modified sgRNA and/or increased specificity of the modified sgRNA for the target nucleic acid. In some embodiments, the target nucleic acid comprises a target DNA or a target RNA. Gene regulation of a target nucleic acid encompasses any mechanism used by cells to increase or decrease the production of a specific gene product (e.g., protein or RNA) by the target nucleic acid and includes efficient genome editing of the target nucleic acid or modulation (e.g., inhibition or activation) of gene expression of the target nucleic acid. In some instances, the gene regulation comprises genome editing of the target DNA. The genome editing can be homologous-directed repair (HDR) or nonhomologous end joining (HEJ) of the target DNA. In other cases, the gene regulation comprises modulating (e.g., inhibiting or activating) gene expression of the target DNA or target RNA using an endonuclease-deficient Cas polypeptide.

The Xenonucleic acids used in the invention are new nucleic acid molecular oligomers that hybridize by Watson-Crick base pairing to target DNA sequences yet have a modified chemical backbone. The xenonucleic acid oligomers are highly effective at hybridizing to target sequences and can be employed as molecular clamps in quantitative real-time polymerase chain reactions or as highly specific molecular probes for detection of nucleic acid target sequences.

This invention is also based, at least in part, on an unexpected discovery that certain chemical modifications to gRNA are tolerated by the CRISPR-Cas system. In particular, certain chemical modifications believed to increase the stability of the gRNA, to alter the thermostability of a gRNA hybridization interaction, and/or to decrease the off-target effects of Cas:gRNA complexation do not substantially compromise the efficacy of Cas:gRNA binding to, nicking of, and/or cleavage of the target polynucleotide. Furthermore, certain chemical modifications are believed to provide gRNA, including sgRNA, having efficient and titratable transfectability into cells, especially into the nuclei of eukaryotic cells, and/or having minimal or no immunostimulatory properties in the transfected cells. Certain chemical modifications are believed to provide gRNA, including sgRNA, which can be effectively delivered into and maintained in the intended cell, tissue, bodily fluid or organism for a duration sufficient to allow the desired gRNA functionality.

For purposes of illustration, the scheme below illustrates the differences between DNA and XNA:

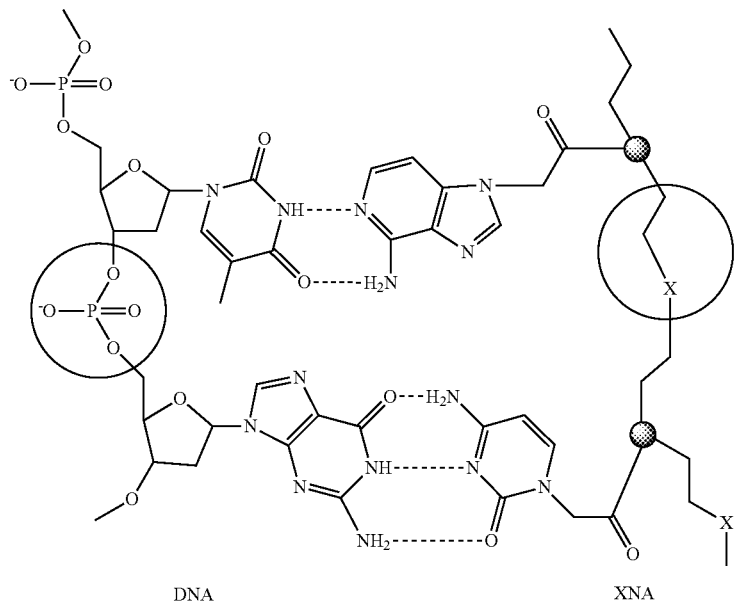

DNA  XNA

Applicant has developed a multitude of XNA chemistry and multiple applications of XNA in molecular testing including, PCR-Clamping, in-situ detection of gene mutations and targeted CRISPR/Cas9 gene-editing and detection. Applicant's XNA chemistry is unique in that a single nucleotide change in the target sequence can lead to a melting temperature differential of as much as 15-200 C. For natural DNA the Tm differential for such a change is only 5-70 C.

Representative examples are shown below:
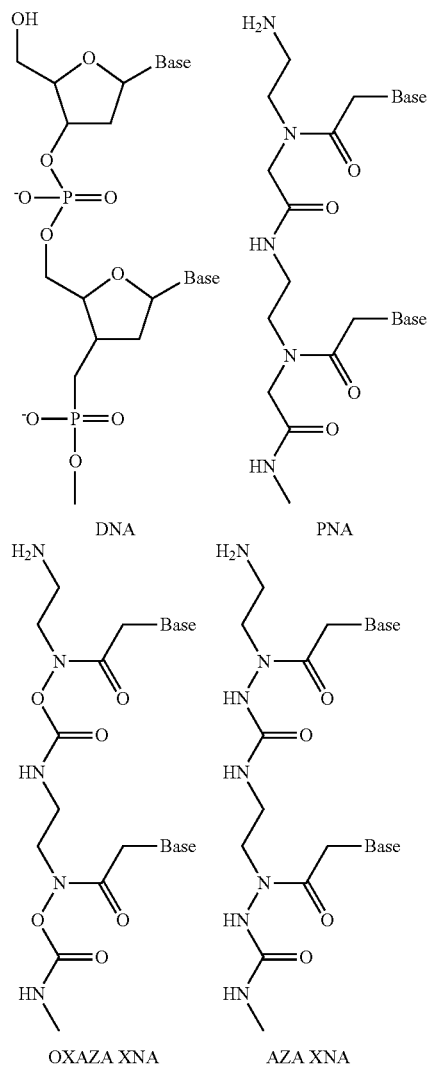
The XNA monomers are synthesized as shown in the following schemes:
Synthesis of Xenonucleic Acid (XNA) Monomers
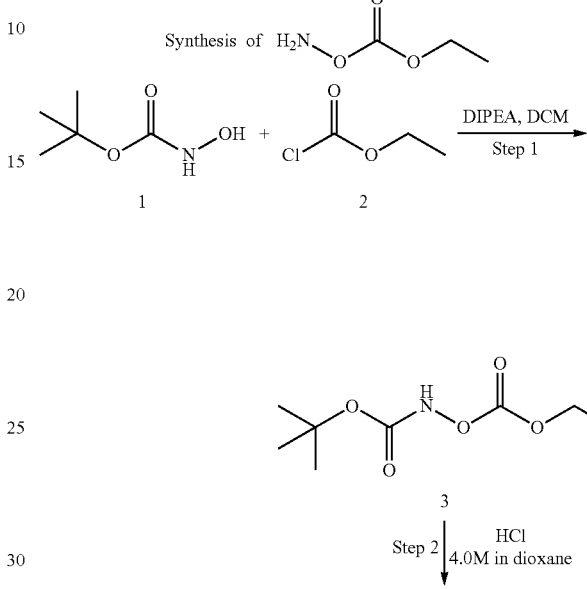
Aza-XNA Monomer Synthesis
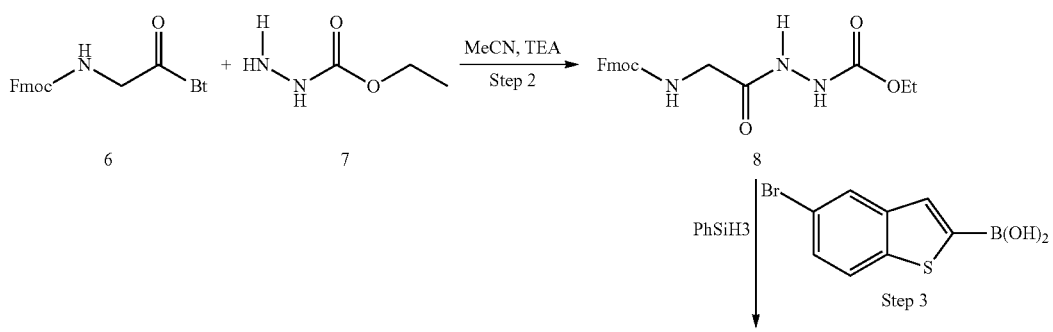

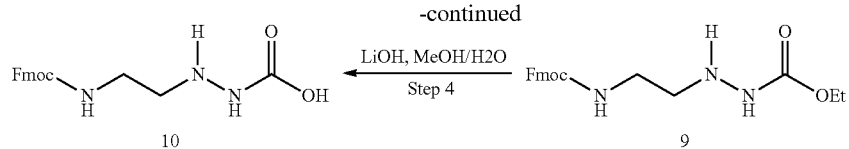
Synthesis of Oxaza-XNA Monomer
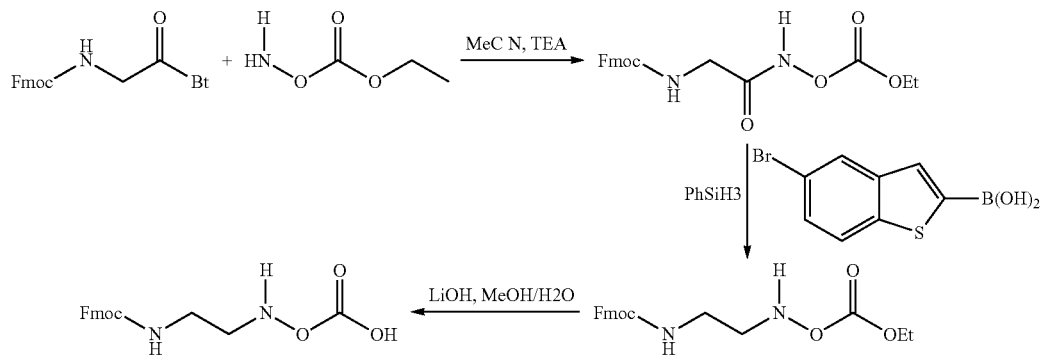
Attachment of Protected Nucleic Acid Bases and Solid Phase Synthesis of XNA Oligomers
Benzothiazole-2-Sulfonyl-(Bts) Route to XNA Monomer Synthesis
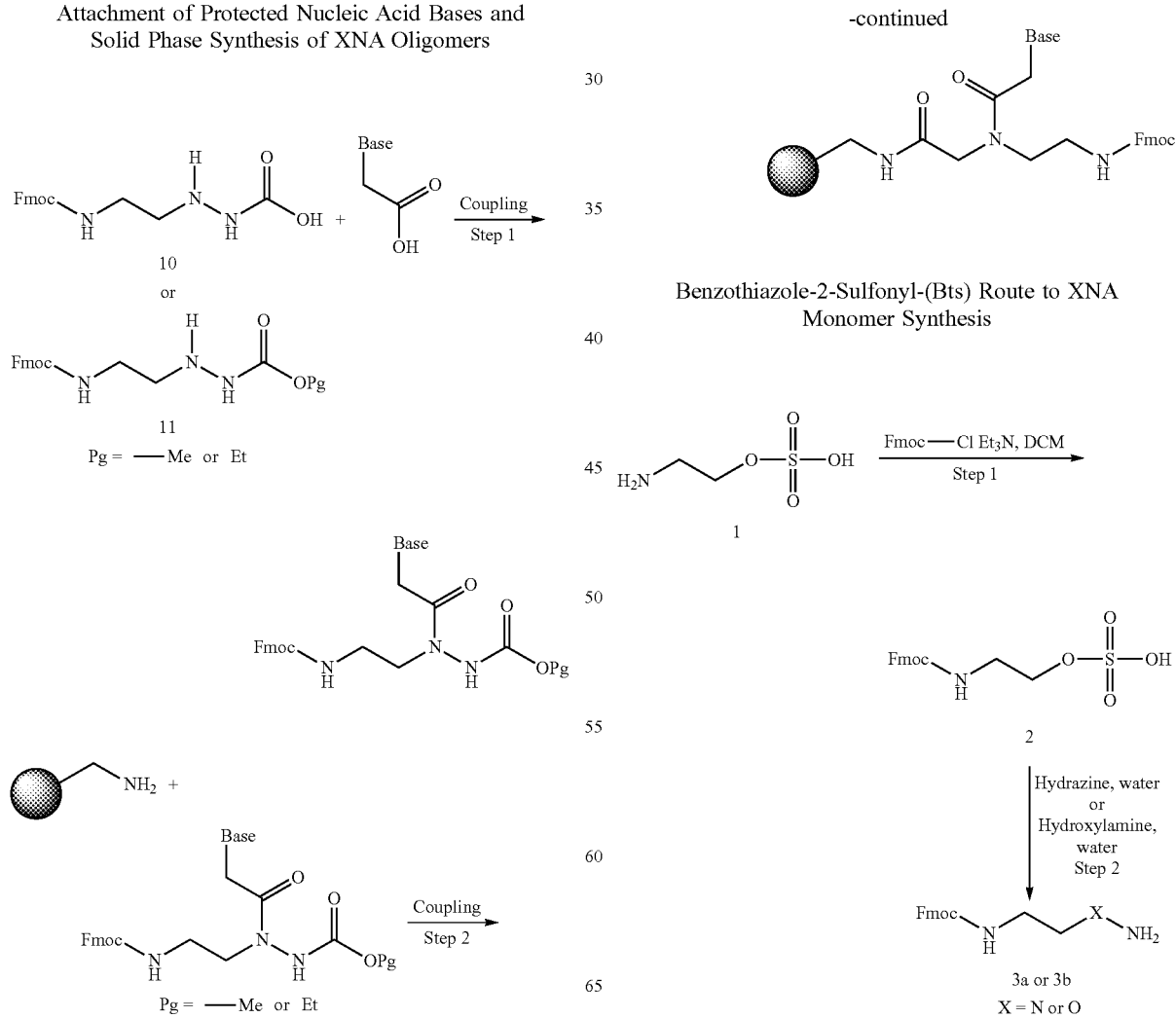

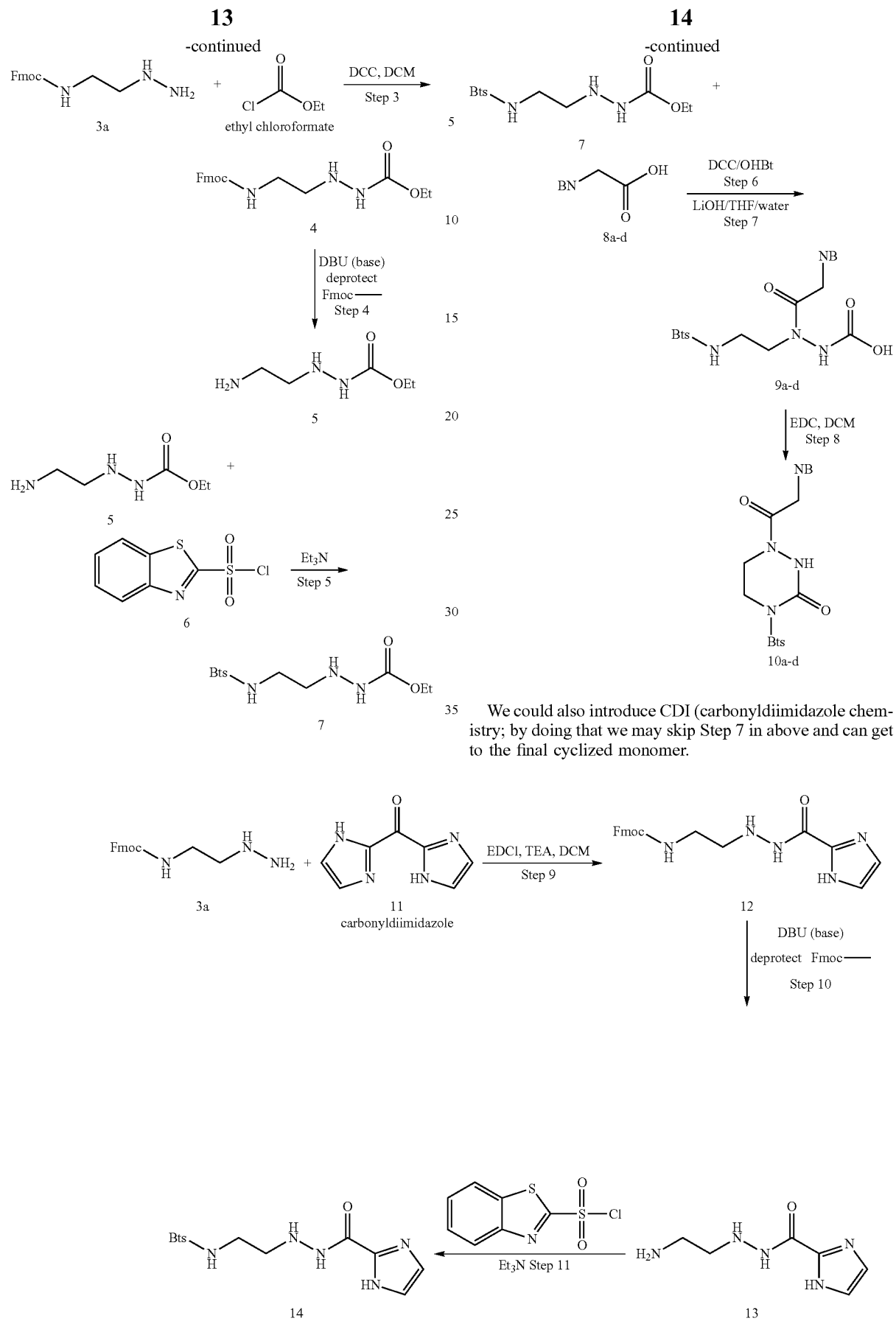
We could also introduce CDI (carbonyldiimidazole chemistry; by doing that we may skip Step 7 in above and can get to the final cyclized monomer.

-continued

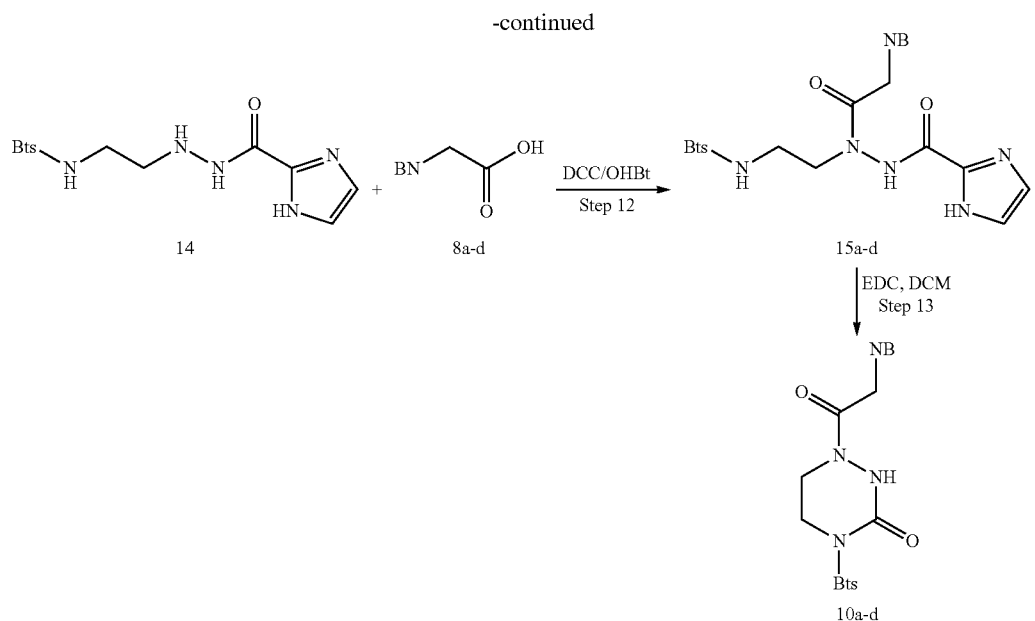

The azide derivatized XNA is made via azidobutyrate NHS ester can be used to introduce an active azide group to an amino-modified oligonucleotide. Introduction can be done at either the 5'- or 3'-end, or internally. To do this, the oligo first must be synthesized with a primary amino functional group modification, e.g. amino $C_6$ for the 5' end or amino $C_7$ for the 3' end for the ends) or the amino $C_6$ version of the base phosphoramidite (for internal labeling). The Azidobutyrate NHS ester is then manually attached to the oligo through the amino group in a separate reaction post-synthesis. The presence of the azide allows the user to use "Click Chemistry" (a [3+2] cycloaddition reaction between alkynes and azides, using copper (I) iodide as a catalyst) to conjugate the azide-modified oligo to a terminal alkyne-modified oligo with extremely high regioselectivity and efficiency.

A representative chemical structure is as follows:

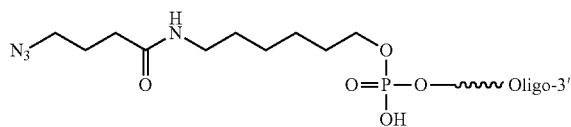

In one embodiment, the XNA-gRNA chimera are synthesized by chemical coupling of 3'-modified XNA oligomer with a suitable 5'-modified synthetic RNA oligomer using conjugation chemistries that are well known in the art. An example as mentioned above is "Click chemistry" utilizing alkynyl modified linkers and/or nucleosides and azide modified linkers for attachment.

Click chemistry involves the rapid generation of compounds by joining small units together via heteroatom links (C-X-C). The main objective of click chemistry is to develop a set of powerful, selective, and modular "blocks" that are useful for small- and large-scale applications. Reaction processes involved in click chemistry should conform to a defined set of stringent criteria such as being: Simple to perform, modular, wide in scope, high yielding, stereospecific, environmentally friendly by generating only harmless byproducts that can be removed by non-chromatographic methods.

Important characteristics of the reactions involved in click chemistry are: simple reaction conditions, readily and easily available starting materials and reagents, use of no solvent, a benign solvent (such as water), or one that is easily removed, simple product isolation and product should be stable under physiological conditions.

Click chemistry involves the use of a modular approach and has important applications in the field of drug discovery, combinatorial chemistry, target-templated in situ chemistry, and DNA research.

A well-known click reaction is the Huisgen 1,3-dipolar cycloaddition of azides and alkynes. This reaction, yielding triazoles, has become the gold standard of click chemistry for its reliability, specificity, and biocompatibility. Such cycloadditions need high temperatures or pressures when the reaction involves simpler alkene or azides, since the activation energies are high ($\Delta G^{\square} \approx +26$ kcal/mol). Sharpless & co-workers and Meldal & co-workers reported Cu(I) catalysts expedite the reaction of terminal alkynes and azides, thereby affording 1,4-disubstituted triazoles. This reaction is an ideal click reaction and is widely employed in material science, medicinal chemistry, and chemical biology.

The Scheme of the well-known Cu-catalyzed azide-alkyne cycloaddition reaction:

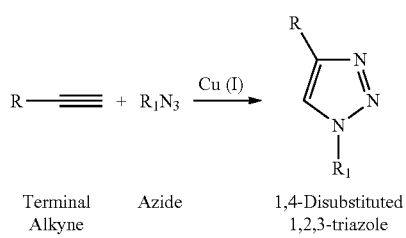

| Terminal Alkyne | Azide | 1,4-Disubstituted 1,2,3-triazole |

The cytotoxic nature of transition metals, employed as catalysts for the click reactions, precluded their use for in vivo applications. Alternative approaches with lower activation barriers and copper-free reactions were proposed. Such reactions were referred to as "copper-free click chemistry". Copper-free click chemistry is based on a very old reaction, published in 1961 by Wittig et al. It involved the reaction between cyclooctyne and phenyl azide, which proceeded like an explosion to give a single product, 1-phenyl-4,5,6,7,8,9-hexahydro-1H-cycloocta[d][1,2,3]triazole. The reaction is ultrafast due to the large amount of ring-strain (18 kcal/mol of ring strain) in the cyclooctyne molecule. Release of the ring-strain in the molecule drives the fast reaction. Cyclooctynes are reported to react selectively with azides to form regioisomeric mixtures of triazoles at ambient temperatures and pressures without the need for metal catalysis and no apparent cytotoxicity. Difluorinated cyclooctyne reagents have been reported to be useful for the copper-free click chemistry.

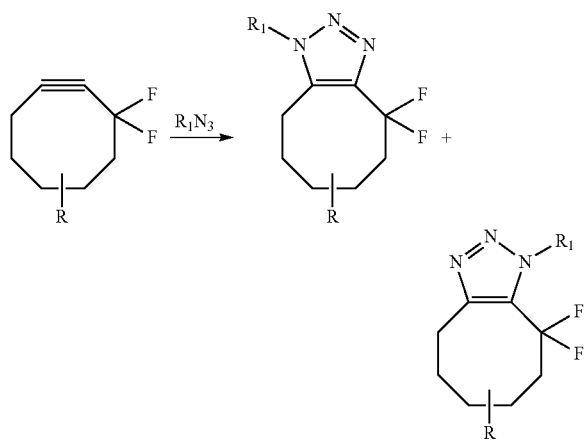

Co-delivering chemically modified sXNA-gRNAs with Cas9 mRNA or protein is an efficient RNA- or ribonucleoprotein (RNP)-based delivery method for the CRISPR-Cas system, without the toxicity associated with DNA delivery. This approach is a simple and effective way to streamline the development of genome editing with the potential to accelerate a wide array of biotechnological and therapeutic applications of the CRISPR-Cas technology.

Very little is known about the tolerance of the gRNAs of Cas9 and Cpf1 towards chemical modifications. Without this information, it is challenging to rationally engineer gRNAs for biotechnological applications. Also 'off-target' binding of crRNA's is a problem for specificity of targeted NHEJ or HDR mediated editing.

Thus we generated chemically modified CRISPR targeting RNAs (crRNAs), which had XNA or donor DNA sequence(s) attached at their 5' or 3' ends, and evaluated their ability to cleave genomic DNA, after complexation with Cas9, in cells expressing green fluorescent protein (GFP) under control of the TET on/off promoter system. The constructs consisted of crRNAs targeting the GFP sequence, which had a short single stranded XNA (15-24 nucleobases) or donor DNA (82-87 nucleotides), at their 5' or 3' position. These modifications were chosen because of their importance in performing conjugation reactions.

Figure 4:
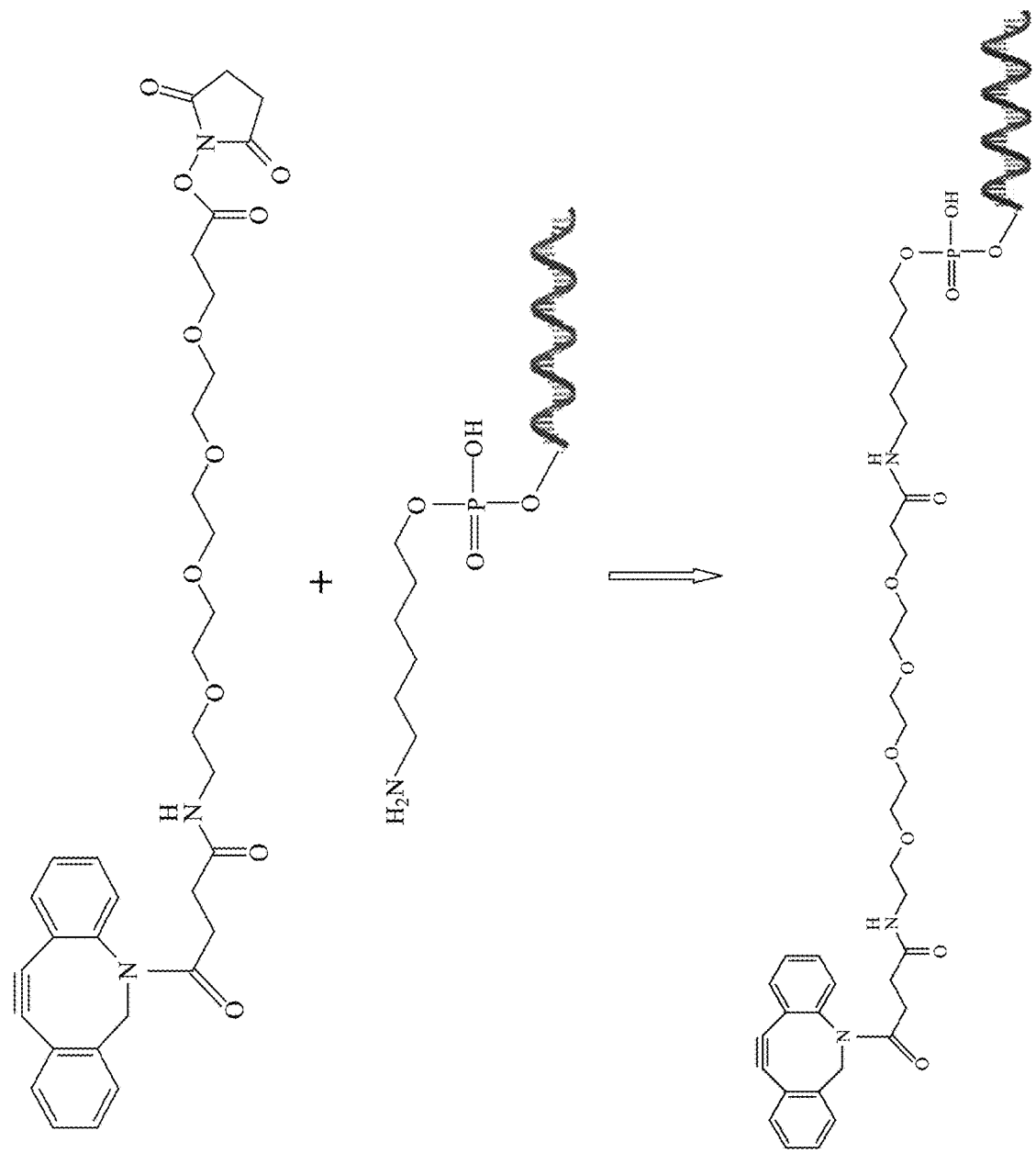
FIGS. 4 and 5 illustrate the synthetic scheme for making the XNA-(linker)-crRNA.
Figure 5:
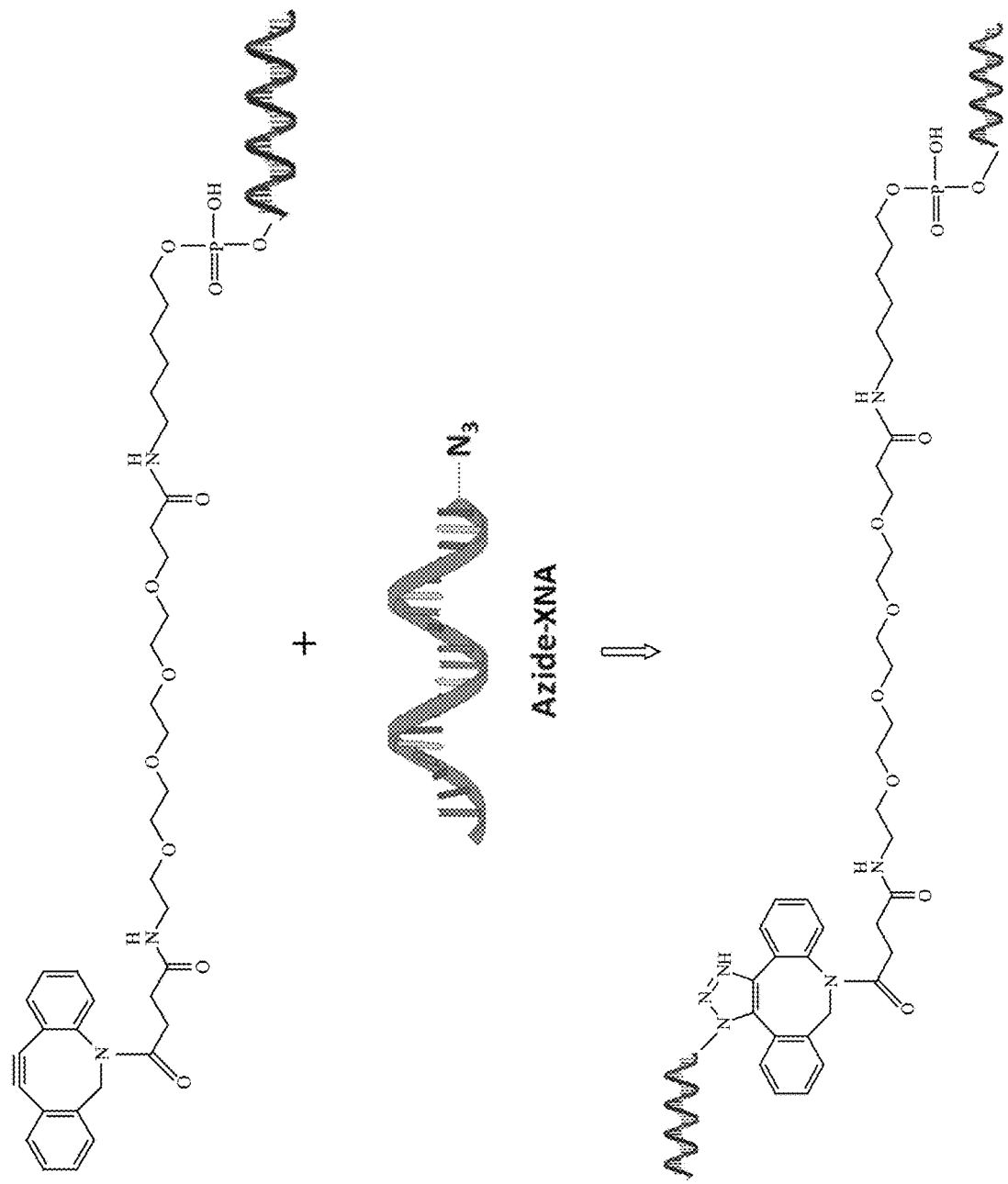

The Exemplary synthesis of a 5'-XNA linked crRNA is shown in FIGS. 4 and 5.

The linker length that is used in the conjugate is determined empirically based on the target binding sequence that is distal (i.e. 5'-upstream of 3' downstream of the CRISPR edit site in the target gene.)

We selected as a target gene to demonstrate the utility of our approach the tetracycline inducible EGFP reporter (TET on/off) system in HEK293 cells. CRISPR gRNA was targeted to inactivate the TET repressor. Efficient generation of deletions in this target region would lead to expression of the EGFP reporter gene which can be measures by fluorescence microscopy and/or FACS analysis For TET repressor EGFP reporter targeted CRISPR/Cas9 mediated gene editing the sequence of the crRNA and tracrRNA is shown below:

CRISPR gRNA:
SEQ ID NO: 1
5'-gUGGACUCAUGAUCACGGGUCGUUUUAGAGCUA-3' tracrRNA:
SEQ ID NO: 2
5'-AGCAAGUUAAAAUAAGGCUAGUCCGUUAUCAACUUG
AAAAGUGGCACCGAGUC GGUGC-3'

TET Repressor EGFP/CRISPR/Cas9 Target Site:
SEQ ID NO: 3
PAM    I Cut Site
AGATCTACCATGCCAAAGAGACCCAGACCCGTGATCATGAGTCCAAAGA
GAAGAACACAGGCAGAGCGCGCAATGGAGACCCAG SEQ ID NO: 4
TCTAGATGGTACGGTTTCTCTGGGTCTGGGCACTAGTACTCAGGTTTCT
CTTCTTGTGTCCGTCTCGCGCGTTACCTCTGGGTC
gRNA CRISPR/Cas9 disruption of the TET repressor leads to inducible expression of EGFP reporter in HEK293 cells. The % modification is measured employing detection of EGFP expression in the presence of tetracycline. High EGFP expression implies efficient KO of the TET repressor by CRISPR/Cas9. FIG. 2 shows that synthetic sXNA-crRNA is much more efficient than scrRNA alone and radically more efficient that plasmid derived crRNA.

Additional CRISPR gene-editing target xeno-clamp sequences that can be used in the present invention include: GBP1 edit site clamp, SEQ ID NO: 5 D-LYS-O-AGAGTTGTGTCGTCGA;
Wild-type xeno-clamp for a target gene, SEQ ID NO: 6 D-LYS-O-TTTCTACGCTCAGCCTT GG;
Mutant specific xeno-clamp for a target gene, SEQ ID NO: 7 D-LYS-O-TTTCTCCGCTCAGCC TTGG Clamp (1) is for a gene: GBP1 that is responsible for development of resistance to therapy in ovarian cancer. Clamps (2) and (3) are designed to be used when the target gene to be edited is a heterozygote i.e. the target site has a heterozygous mutation in the vicinity of the CRISPR edit site! So it is very difficult to determine editing efficiency since the target gene already has an endonuclease cleavage site present even before CRISPR editing. Using wild-type and mutant specific clamps is the only way to determine editing efficiency.

Other xenoclamps include:
WTAP CRISPR target (NEB), SEQ ID NO: 8 AcACC-CACAGTTCGATT-NH$_2$ and GFP gene editing site XNA clamp sequence, SEQ ID NO: 9 5'-D-LYS-O-CCGGTCAGCTCG AT-3'.

Additional xenoclamps that can be used in the invention include oxy-aza and aza XNAs described in the table below.

| Sequence Name | | | Oxy-Aza | Aza XNA |
|---|---|---|---|---|
| BR001 | SEQ ID NO: 10 | ATCGAGATTTCACTGTAGCTAGAC | x | |
| DPCA001 | SEQ ID NO: 11 | ACTTCAGGCAGCGTCTTCA | | x |
| DPCA002 | SEQ ID NO: 12 | TGTTCAGAGCACACTTCAG | | x |
| DPCA003 | SEQ ID NO: 13 | CTGGTGGTTGAATTTGCTG | | x |
| DPCA004 | SEQ ID NO: 14 | CATGAGCTCCAGCAGGATGAAC | | x |
| DPCA005 | SEQ ID NO: 15 | CCGAAGTCTCCAATCTTGG | | x |
| DPCA006 | SEQ ID NO: 16 | TAGATGTCTCGGGCCATCC | | x |
| DPCBRC001 | SEQ ID NO: 17 | GGGACACTCTAAGAT | x | |
| DPCBRC002 | SEQ ID NO: 18 | TTCTGTCCTGGGATTCTC | x | |
| DPCBRC003 | SEQ ID NO: 19 | AGATTTTCCACTTGCTGT | x | |
| DPCBRCA001-2 | SEQ ID NO: 20 | CCAGATGGGACACTCTAAGATTTTC | x | |
| DPCBRCA002-2 | SEQ ID NO: 21 | CCTTTCTGTCCTGGGATTCTCTT | x | |
| DPCBRCA003-2 | SEQ ID NO: 22 | GACAGATTTTCCACTTGCTGTGCTAA | x | |
| DPCBRCA004 | SEQ ID NO: 23 | CATAAAGGACACTGTGAAGGCC | x | |
| DPCBRCA004B | SEQ ID NO: 24 | D-LYS-O-GGCCTTCACAGTGTCCTTTA TG | x | |
| DPCCKT002 | SEQ ID NO: 25 | D-LYS-O-CATTCTTGATGTCTCTGGCT AG | | x |
| DPCE001 | SEQ ID NO: 26 | GAGCCCAGCACTTT | x | |
| DPCE001B | SEQ ID NO: 27 | D-LYS-O-CGGAGCCCAGCACTTTGAT | x | |
| DPCE001B1 | SEQ ID NO: 28 | D-LYS-O-CGGAGCCCAGCACTTTGAT | x | |
| DPCE002 | SEQ ID NO: 29 | NH(2)-AGATGTTGCTTCTCTTAA-CONH(2) | x | |
| DPCE002B | SEQ ID NO: 30 | D-LYS-O-AGATGTTGCTTCTCTTAA | x | |
| DPCE002C | SEQ ID NO: 31 | D-LYS-O-CGGAGATGTTGCTTCTCTTAATTCC | x | |
| DPCE004 | SEQ ID NO: 32 | CAGTTTGGCCAGCCCA | x | |
| DPCE004B | SEQ ID NO: 33 | CAGTTTGGCCAGCCCA-O-D-LYS | x | |
| DPCE004C | SEQ ID NO: 34 | D-LYS-O-TTTGGCCAGCCCAAAATCTGT | x | |
| DPCE004D | SEQ ID NO: 35 | D-LYS-O-GGCCAGCCCAAAATCTGT | x | |
| DPCE005 | SEQ ID NO: 36 | ACCCAGCAGTTTGGC | x | |
| DPCE005B | SEQ ID NO: 37 | D-LYS-O-ACCCAGCAGTTTGGC | x | |
| DPCE006 | SEQ ID NO: 38 | GCTGCGTGATGAG | x | |
| DPCE007 | SEQ ID NO: 39 | GCTGCGTGATGA | x | |
| DPCE008 | SEQ ID NO: 40 | AGCTCATCACGCAGCTCATG | | x |
| DPCE008B | SEQ ID NO: 41 | D-LYS-O-CAGCTCATCACGCAGCTCATGC | | x |
| DPCE008C | SEQ ID NO: 42 | D-LYS-O-TCATCACGCAGCTCATGCCCTT | | x |
| DPCE008D | SEQ ID NO: 43 | D-LYS-O-CTCATCACGCAGCTCATG | | x |
| DPCE008E | SEQ ID NO: 44 | D-LYS-O-TGAGCTGCGTGATG | | x |
| DPCE009B | SEQ ID NO: 45 | D-LYS-O-TCCACGCTGGCCATCACGTA | x | |
| DPCE009B-1 | SEQ ID NO: 46 | TCCACGCTGGCCATCACGTA-O-D-LYS | x | |
| DPCE010B | SEQ ID NO: 47 | TGGGGGTTGTCCAC-O-D-LYS | x | |
| DPCE011 | SEQ ID NO: 48 | GCACACGTGGGGGTT-O-D-LYS | x | |
| DPCE012 | SEQ ID NO: 49 | D-LYS-O-ACAACCCCCACGTGTGC | x | |

| Sequence Name | | | Oxy-Aza | Aza | XNA |
|---|---|---|---|---|---|
| DPCH001 | SEQ ID NO: 50 | CTGAGCCAGGAGAAAC | x | | |
| DPCH002 | SEQ ID NO: 51 | GTAAACTGAGCCAGGAG | x | | |
| DPCH003 | SEQ ID NO: 52 | ATGGCACTAGTAAACTGAGC | x | | |
| DPCH004 | SEQ ID NO: 53 | ATCCATATAACTGAAAGCCAA | x | | |
| DPCH005 | SEQ ID NO: 54 | ACCACATCATCCATATAACTGAA | x | | |
| DPCHRAS001B | SEQ ID NO: 55 | D-LYS-O-O-TTGCCCACACCGCCGGC | x | | |
| DPCHRAS002 | SEQ ID NO: 56 | D-LYS-O-O-TCTTGCCCACACCGCC | x | | |
| DPCHRAS003 | SEQ ID NO: 57 | D-LYS-O-O-TACTCCTCCTGGCCGGC | x | | |
| DPCJ001 | SEQ ID NO: 58 | CGTCTCCACAGACACATACTCCA | x | | |
| DPCJ002B | SEQ ID NO: 59 | CGTCTCCACAGACACATACTCCA-O-D-LYS | x | | |
| DPCK001B | SEQ ID NO: 60 | GCCTACGCCACCAGCTCCAAC-O-D-LYS | x | | |
| DPCK001B2 | SEQ ID NO: 61 | GCCTACGCCACCAGCTCCAAC-O-O-D-LYS | x | | |
| DPCK001C | SEQ ID NO: 62 | CTACGCCACCAGCTCCAACTACCA | x | | |
| DPCK001C2 | SEQ ID NO: 63 | CTACGCCACCAGCTCCAACTACCA-O-D-LYS | x | | |
| DPCK002 | SEQ ID NO: 64 | TCTTGCCTACGCCACCAGCTCCA | x | | |
| DPCK003 | SEQ ID NO: 65 | TGTACTCCTCTTGACCTGCTGTG | x | | |
| DPCK003B | SEQ ID NO: 66 | D-LYS-O-TGTACTCCTCTTGACCTGCTGTG | x | | |
| DPCK004 | SEQ ID NO: 67 | NH(2)-GGCAAATCACATTTATTTCCTAC-CONH(2) | x | | |
| DPCK004B | SEQ ID NO: 68 | D-LYS-O-GGCAAATCACATTTATTTCCTAC | x | | |
| DPCK005B | SEQ ID NO: 69 | D-LYS-O-TGTCTTGTCTTTGCTGATGTTTC | x | | |
| DPCK005 | SEQ ID NO: 70 | TGTCTTGTCTTTGCTGATGTTTC | x | | |
| DPCK005C | SEQ ID NO: 71 | D-LYS-O-TGTCTTGTCTTTGCTGATGTTTC | x | | |
| DPCK006 | SEQ ID NO: 72 | NH(2)-CTCTTGACCTGCTGTGTCGAG-CONH(2) | x | | |
| DPCN001 | SEQ ID NO: 73 | TCCCAACACCACCTGCTCCAA | x | | |
| DPCN001B | SEQ ID NO: 74 | D-LYS-O-CAACACCACCTGCTCCAACCACCAC | x | | |
| DPCN002 | SEQ ID NO: 75 | CTTTTCCCAACACCACCTGCTCC | x | | |
| DPCN002B | SEQ ID NO: 76 | D-LYS-O-TGCGCTTTTCCCAACACCACCTGCT | x | | |
| DPCN003B | SEQ ID NO: 77 | GGCACTGTACTCTTCTTGTCCAG | x | | |
| DPCN004B | SEQ ID NO: 78 | D-LYS-O-TCTGGTCTTGGCTGAGGTTTC | x | | |
| DPCN006 | SEQ ID NO: 79 | NH(2)-GGCAAATCACACTTGTTTCCCAC-CONH(2) | x | | |
| DPCN006B | SEQ ID NO: 80 | D-LYS-O-GGCAAATCACACTTGTTTCCCAC | x | | |
| DPCN007 | SEQ ID NO: 81 | NH(2)-TTCTTGTCCAGCTGTATCCAGTATG-CONH(2) | x | | |
| DPCPKA003B | SEQ ID NO: 82 | D-LYS-O-AGATCCTCTCTCTGAAATCAC | x | | |
| DPCPKA004 | SEQ ID NO: 83 | D-LYS-O-TCTTTCTCCTGCTCAGTGATTTCA | x | | |
| DPCPKA005 | SEQ ID NO: 84 | D-LYS-O-AATGATGCACATCATGGTGGCTG | x | | |
| NRASN003C | SEQ ID NO: 85 | D-LYS-O-GGCACTGTACTCTTCTTGTCCAG | x | | |
| QMDXNA001 | SEQ ID NO: 86 | NH(2)-O-TTCATCAACCGCACTCTGTTTATCTC | | | x |
| QMDXNA002 | SEQ ID NO: 87 | NH(2)-O-TGGCGACGACAATGGACCCAATTAT | | | x |

| Sequence Name | | | Oxy-Aza | Aza XNA |
|---|---|---|---|---|
| QMDXNA003 | SEQ ID NO: 88 | NH(2)-O-AGATGTAGTTAGCAATCGGTCCTTGTTGTA | | x |
| QMDXNA004 | SEQ ID NO: 89 | NH(2)-O-GGGTAATTGAGGTAACGTAGGTATCAAGAT | | x |
| QMDXNA005 | SEQ ID NO: 90 | NH(2)-O-TACTATCGACTGACATGAGGCTTGTGT | | x |
| XNADE001 | SEQ ID NO: 91 | D-LYS-O-AGTCCGACGATCTGGAATTC | | x |
| XNADE002 | SEQ ID NO: 92 | D-LYS-O-ACTGGAGTTCAGACGTGTG | | x |
| XNADE003 | SEQ ID NO: 93 | D-LYS-O-CTCTTCCGATCAGATCGGAA | | x |
| XNADE003b | SEQ ID NO: 94 | D-LYS-O-CTCTTCCGATCAGATCGGAAG | | x |
| XNAFGFR001 | SEQ ID NO: 95 | D-LYS-O-O-AGCGCTCCCCGCACC | x | |
| XNAFGFR001 | SEQ ID NO: 96 | D-LYS-O-O-AGCGCTCCCCGCACC | x | |
| XNAFGFR002 | SEQ ID NO: 97 | D-LYS-O-GGGGAGCGCTCTGT-O-TTTTT | x | |
| XNAFGFR003 | SEQ ID NO: 98 | D-LYS-O-O-AGCGCTCCCCGCACC-O-TTTTTT | x | |
| XNAFGFR004 | SEQ ID NO: 99 | D-LYS-O-TGCATACACACTGCCCGCCT | x | |

EXAMPLES

Click chemistry is a versatile reaction that can be used for the synthesis of a variety of conjugates. Virtually any biomolecules can be involved, and labeling with small molecules, such as fluorescent dyes, biotin, and other groups can be readily achieved.

Click chemistry reaction takes place between two components: azide and alkyne (terminal acetylene). Both azido and alkyne groups are nearly never encountered in natural biomolecules. Hence, the reaction is highly bioorthogonal and specific. If there is a need to label an oligonucleotide, alkyne-modified oligonucleotides can be ordered at many of the custom oligo-synthesizing facilities and companies.

We recommend using the following general protocol for Click chemistry labeling of alkyne-modified oligonucleotides with azides produced by Lumiprobe Corp. The auxiliary reagents can be ordered at Lumiprobe Corp.

1. Calculate the volumes of reagents required for Click chemistry labeling using the table below. Prepare the required stock solutions.

| Reagent | Final concentration in the mixture | Stock solution concentration |
|---|---|---|
| Oligonucleotide, alkyne-modified | Varies (20-200 uM) | varies |
| Azide | 1.5 × (oligonucleotide concentration) | 10 mM in DMSO |
| DMSO | 50 vol % | — |
| Ascorbic acid | 0.5 mM | 5 mM in water |
| Cu-TBTA complex | 0.5 mM | 10 mM in 55 vol % DMSO |

1. Dissolve alkyne-modified oligonucleotide or DNA in water in a pressure-tight vial.
2. Add 2M triethylammonium acetate buffer, pH 7.0, to final concentration 0.2 M.
3. Add DMSO, and vortex.
4. Add azide stock solution (10 mM in DMSO), and vortex.
5. Add the required volume of 5 mM Ascorbic Acid Stock solution to the mixture, and vortex briefly.
6. Degass the solution by bubbling inert gas in it for 30 seconds. Nitrogen, argon, or helium can be used.
7. Add the required amount of 10 mM Copper (II)-TBTA Stock in 55% DMSO to the mixture. Flush the vial with inert gas and close the cap.
8. Vortex the mixture thoroughly. If significant precipitation of azide is observed, heat the vial for 3 minutes at 80° C., and vortex.
9. Keep at room temperature overnight.
10. Precipitate the conjugate with acetone (for oligonucleotides) or with ethanol (for DNA). Add at least 4-fold volume of acetone to the mixture (If the volume of the mixture is large, split in several vials). Mix thoroughly and keep at −20° C. for 20 minutes.
11. Centrifuge at 10000 rpm for 10 minutes.
12. Discard the supernatant.
13. Wash the pellet with acetone (1 mL), centrifuge at 10000 rpm for 10 minutes.
14. Discard the supernatant, dry the pellet, and purify the conjugate by RP-HPLC or PAGE.

XNA-crRNA Synthesis and Purification

XNA(s) containing 3'-azide monomer were synthesized on a 5-μmol scale on an Applied Biosystems 433A peptide synthesizer. Resin used was NovaSyn TGR (rink amide) resin preloaded with FMoc-D-lysine (substitution 0.045 meq/g). 3'-azido-XNA (10 mM) was mixed with 5'-DBCO-crRNA (30 mM) in DI water (50 mL). The solution was incubated at room temperature over-night and the unreacted crRNA was removed by running the reaction solution through a 30k concentrator (Amicon Ultra, EMD Millipore). The XNA-crRNA reaction solution was analyzed via gel electrophoresis using a polyacrylamide gel (4-20% Mini-protean TGX Precast gel, Biorad) 200 ng of the reaction mixture was loaded into the gel. The XNA-crRNA band was cut with a sharp knife and eluted using the crush and soak method in nuclease-free water for 16 hr, and isolated via ethanol precipitation.

NanoFect™ Transfection Reagent (Alstem, Cat #NF100)

The following protocol was used for transfection in a 24-well plate.

1. For each well, add 0.5 ml of normal growth medium (antibiotic does not influence the result) freshly 2 hours before transfection.
2. For each well, dilute 0.5 μg of DNA in 50 μl of DMEM without serum, and mix gently.

3. Add 1.5 µl of NanoFect™ reagent (ALSTEM, Cat. #NF100) into another tube with 50 µl of DMEM without serum, and mix gently.
4. Add NanoFect™/DMEM into DNA/DMEM solution. Mix by vortexing for 5-10 seconds.
5. Incubate for ~15 minutes at room temperature to allow for NanoFect™/DNA complexes self-assembly.
6. Add the 100 µl NanoFect™/DNA mix drop-wise to the cells in each well and homogenize by gently swirling the plate.
7. Return the plates to the cell culture incubator.
8. Check transfection efficiency under fluorescent microscopy or FACS sorting cells 24 to 48 hours post transfection.

REFERENCES

1) Chemically modified guide RNAs enhance CRISPR-Cas genome editing in human primary cells. A. Hendel et. al., Nature Biotechnology 2015, 33, 985-989 DOI: 10.1038/nbt.3290
2) Site-specific terminal and internal labeling of RNA by poly(A) polymerase tailing and copper-catalyzed or copper-free strain-promoted click chemistry. M.-L. Winz et. al., Nucleic Acids Research, 2012, 1-13 DOI:10.1093/nar/gks062
3) A. V. Ustinov, I. A. Stepanova, V. V. Dubnyakova, T. S. Zatsepin, E. V. Nozhevnikova, V. A. Korshun. Modification of nucleic acids using [3+2]-dipolar cycloaddition of azides and alkynes. Russ. J. Bioorg. Chem. 36(4), 401-445 (2010). DOI: 10.1134/S1068162010040011
4) A. H. El-Sagheer, T. Brown. Click chemistry with DNA. Chem. Soc. Rev. 39(4), 1388-1405 (2010). DOI: 10.1039/B901971P
5) F. Amblard, J. H. Cho, R. F. Schinazi. Cu(I)-catalyzed Huisgen azide-alkyne 1,3-dipolar cycloaddition reaction in nucleoside, nucleotide, and oligonucleotide chemistry. Chem. Rev. 109(9), 4207-4220 (2009). DOI: 10.1021/cr9001462
6) F. Zhang et. al., Genome engineering using the CRISPR-Cas9 system Nature Protocols, 2013, 8 (11), 2281-2308

The content of all references cited in the instant specification and all cited references in each of those references are incorporated in their entirety by reference herein as if those references were denoted in the text While the many embodiments of the invention have been disclosed (Angres) above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. RNA modified with a linker and a xenonucleic acid wherein said xenonucleic acid has chemical functionality selected from the group consisting of oxaza and aza and wherein said xenonucleic acid is represented structurally by the following formulas

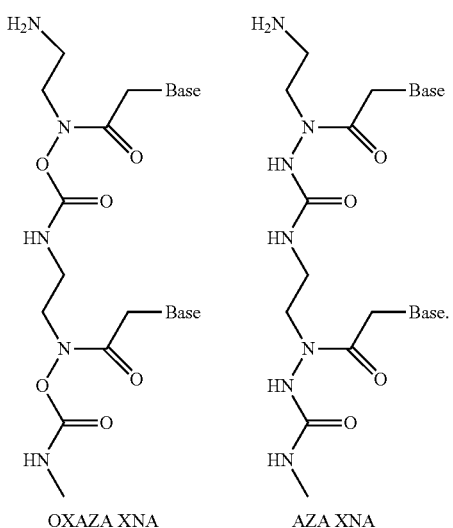

OXAZA XNA      AZA XNA

2. The modified RNA of claim 1, wherein said RNA is sgRNA.

3. The modified RNA of claim 1, wherein said RNA is crRNA.

4. The modified RNA of claim 1, wherein said RNA is tracrRNA.

5. The modified RNA of claim 1, wherein said RNA is chimeric.

6. A method for inducing gene regulation of a target nucleic acid in a primary cell, the method comprising: introducing into the primary cell:
   (a) a xenonucleic acid modified single guide RNA (sgRNA) comprising a first nucleotide sequence that is complementary to the target nucleic acid and a second nucleotide sequence that interacts with a CRISPR-associated protein (Cas) polypeptide, wherein one or more of the nucleotides in the first nucleotide sequence and/or the second nucleotide sequence are nucleotides which have been chemically modified with xenonucleic acids; and
   (b) a Cas polypeptide, an mRNA encoding a Cas polypeptide, and/or a recombinant expression vector comprising a nucleotide sequence encoding a Cas polypeptide, wherein the xenonucleic acid modified sgRNA guides the Cas polypeptide to the target nucleic acid, and wherein the xenonucleic acid modified sgRNA induces gene regulation of the target nucleic acid with an enhanced activity and efficiency relative to a corresponding unmodified sgRNA and wherein said xenonucleic acid is represented structurally by the following formulas

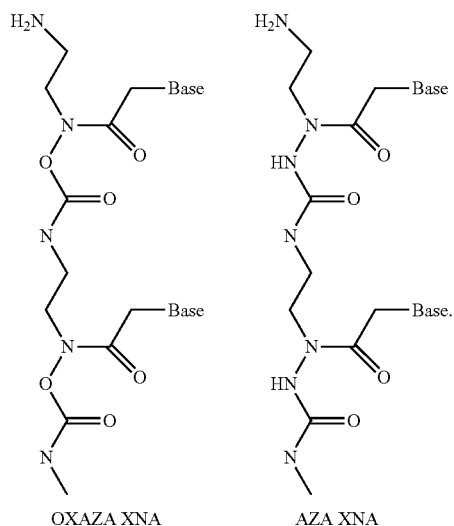

OXAZA XNA      AZA XNA

7. A method for treating a genetic disease in a subject or a plant, the method comprising:
   administering to the subject or plant a xenonucleic acid modified single guide RNA (sgRNA) in a sufficient amount to correct a mutation in a target gene associated with the genetic disease, wherein the xenonucleic acid modified sgRNA comprises a first nucleotide sequence that is complementary to the target gene and a second nucleotide sequence that interacts with a CRISPR-associated protein (Cas) polypeptide, and wherein one or more of the nucleotides in the first nucleotide sequence and/or the second nucleotide sequence are xenonucleic acid modified nucleotides and wherein said xenonucleic acid is represented structurally by the following formulas

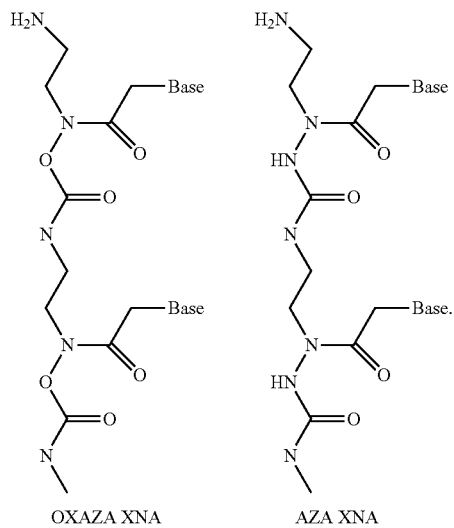

OXAZA XNA      AZA XNA

* * * * *

SEQUENCE LISTING

```
<160> NUMBER OF SEQ ID NOS: 99

<210> SEQ ID NO 1
<211> LENGTH: 32
<212> TYPE: RNA
<213> ORGANISM: Artificial
<220> FEATURE:
<223> OTHER INFORMATION: Synthetic

<400> SEQUENCE: 1
uggacucaug aucacggguc guuuuagagc ua                            32

<210> SEQ ID NO 2
<211> LENGTH: 60
<212> TYPE: RNA
<213> ORGANISM: Artificial
<220> FEATURE:
<223> OTHER INFORMATION: Synthetic

<400> SEQUENCE: 2
uagcaaguua aaauaaggcu aguccguuau caacuugaaa aaguggcacc gagucggugc    60

<210> SEQ ID NO 3
<211> LENGTH: 84
<212> TYPE: DNA
<213> ORGANISM: Artificial
<220> FEATURE:
<223> OTHER INFORMATION: Synthetic

<400> SEQUENCE: 3
agatctacca tgccaaagag acccagaccc gtgatcatga gtccaaagag aagaacacag    60
gcagagcgcg caatggagac ccag                                         84

<210> SEQ ID NO 4
```

```
<211> LENGTH: 84
<212> TYPE: DNA
<213> ORGANISM: Artificial
<220> FEATURE:
<223> OTHER INFORMATION: Synthetic

<400> SEQUENCE: 4
tctagatggt acggtttctc tgggtctggg cactagtact caggtttctc ttcttgtgtc    60
cgtctcgcgc gttacctctg ggtc                                          84

<210> SEQ ID NO 5
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (1)..(16)
<223> OTHER INFORMATION: D-Lys-modified

<400> SEQUENCE: 5
agagttgtgt cgtcga                                                   16

<210> SEQ ID NO 6
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (1)..(19)
<223> OTHER INFORMATION: D-Lys-modified

<400> SEQUENCE: 6
tttctacgct cagccttgg                                                19

<210> SEQ ID NO 7
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (1)..(19)
<223> OTHER INFORMATION: D-Lys-modified

<400> SEQUENCE: 7
tttctccgct cagccttgg                                                19

<210> SEQ ID NO 8
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: Amino modified

<400> SEQUENCE: 8
acccacagtt cgatt                                                    15

<210> SEQ ID NO 9
<211> LENGTH: 14
```

```
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: (1)..(14)
<223> OTHER INFORMATION: D-Lys-modified

<400> SEQUENCE: 9
ccggtcagct cgat                                                       14

<210> SEQ ID NO 10
<211> LENGTH: 24
<212> TYPE: DNA
<213> ORGANISM: artificial
<220> FEATURE:
<223> OTHER INFORMATION: Synthetic

<400> SEQUENCE: 10
atcgagattt cactgtagct agac                                            24

<210> SEQ ID NO 11
<211> LENGTH: 19
<212> TYPE: DNA
<213> ORGANISM: artificial
<220> FEATURE:
<223> OTHER INFORMATION: Synthetic

<400> SEQUENCE: 11
acttcaggca gcgtcttca                                                  19

<210> SEQ ID NO 12
<211> LENGTH: 19
<212> TYPE: DNA
<213> ORGANISM: artificial
<220> FEATURE:
<223> OTHER INFORMATION: Synthetic

<400> SEQUENCE: 12
tgttcagagc acacttcag                                                  19

<210> SEQ ID NO 13
<211> LENGTH: 19
<212> TYPE: DNA
<213> ORGANISM: artificial
<220> FEATURE:
<223> OTHER INFORMATION: Synthetic

<400> SEQUENCE: 13
ctggtggttg aatttgctg                                                  19

<210> SEQ ID NO 14
<211> LENGTH: 22
<212> TYPE: DNA
<213> ORGANISM: artificial
<220> FEATURE:
<223> OTHER INFORMATION: Synthetic

<400> SEQUENCE: 14
catgagctcc agcaggatga ac                                              22

<210> SEQ ID NO 15
<211> LENGTH: 19
<212> TYPE: DNA
<213> ORGANISM: artificial
<220> FEATURE:
```

<223> OTHER INFORMATION: Synthetic

<400> SEQUENCE: 15
ccgaagtctc caatcttgg                                                19

<210> SEQ ID NO 16
<211> LENGTH: 19
<212> TYPE: DNA
<213> ORGANISM: artificial
<220> FEATURE:
<223> OTHER INFORMATION: Synthetic

<400> SEQUENCE: 16
tagatgtctc gggccatcc                                                19

<210> SEQ ID NO 17
<211> LENGTH: 15
<212> TYPE: DNA
<213> ORGANISM: artificial
<220> FEATURE:
<223> OTHER INFORMATION: Synthetic

<400> SEQUENCE: 17
gggacactct aagat                                                    15

<210> SEQ ID NO 18
<211> LENGTH: 18
<212> TYPE: DNA
<213> ORGANISM: artificial
<220> FEATURE:
<223> OTHER INFORMATION: Synthetic

<400> SEQUENCE: 18
ttctgtcctg ggattctc                                                 18

<210> SEQ ID NO 19
<211> LENGTH: 18
<212> TYPE: DNA
<213> ORGANISM: artificial
<220> FEATURE:
<223> OTHER INFORMATION: Synthetic

<400> SEQUENCE: 19
agattttcca cttgctgt                                                 18

<210> SEQ ID NO 20
<211> LENGTH: 25
<212> TYPE: DNA
<213> ORGANISM: artificial
<220> FEATURE:
<223> OTHER INFORMATION: Synthetic

<400> SEQUENCE: 20
ccagatggga cactctaaga ttttc                                         25

<210> SEQ ID NO 21
<211> LENGTH: 23
<212> TYPE: DNA
<213> ORGANISM: artificial
<220> FEATURE:
<223> OTHER INFORMATION: Synthetic

<400> SEQUENCE: 21
cctttctgtc ctgggattct ctt                                           23

```
<210> SEQ ID NO 22
<211> LENGTH: 26
<212> TYPE: DNA
<213> ORGANISM: artificial
<220> FEATURE:
<223> OTHER INFORMATION: Synthetic

<400> SEQUENCE: 22
gacagatttt ccacttgctg tgctaa                                          26

<210> SEQ ID NO 23
<211> LENGTH: 22
<212> TYPE: DNA
<213> ORGANISM: artificial
<220> FEATURE:
<223> OTHER INFORMATION: Synthetic

<400> SEQUENCE: 23
cataaaggac actgtgaagg cc                                              22

<210> SEQ ID NO 24
<211> LENGTH: 22
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(22)
<223> OTHER INFORMATION: D-Lys-modified

<400> SEQUENCE: 24
ggccttcaca gtgtccttta tg                                              22

<210> SEQ ID NO 25
<211> LENGTH: 22
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(22)
<223> OTHER INFORMATION: D-Lys-modified

<400> SEQUENCE: 25
cattcttgat gtctctggct ag                                              22

<210> SEQ ID NO 26
<211> LENGTH: 14
<212> TYPE: DNA
<213> ORGANISM: artificial
<220> FEATURE:
<223> OTHER INFORMATION: Synthetic

<400> SEQUENCE: 26
gagcccagca cttt                                                       14

<210> SEQ ID NO 27
<211> LENGTH: 19
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(19)
<223> OTHER INFORMATION: D-Lys-modified
```

```
<400> SEQUENCE: 27
cggagcccag cactttgat                                                19

<210> SEQ ID NO 28
<211> LENGTH: 19
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(19)
<223> OTHER INFORMATION: D-Lys-modified

<400> SEQUENCE: 28
cggagcccag cactttgat                                                19

<210> SEQ ID NO 29
<211> LENGTH: 18
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(18)
<223> OTHER INFORMATION: D-Lys-modified

<400> SEQUENCE: 29
agatgttgct tctcttaa                                                 18

<210> SEQ ID NO 30
<211> LENGTH: 18
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(18)
<223> OTHER INFORMATION: D-Lys-modified

<400> SEQUENCE: 30
agatgttgct tctcttaa                                                 18

<210> SEQ ID NO 31
<211> LENGTH: 25
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(25)
<223> OTHER INFORMATION: D-Lys-modified

<400> SEQUENCE: 31
cggagatgtt gcttctctta attcc                                         25

<210> SEQ ID NO 32
<211> LENGTH: 16
<212> TYPE: DNA
<213> ORGANISM: artificial
<220> FEATURE:
<223> OTHER INFORMATION: Synthetic

<400> SEQUENCE: 32
cagtttggcc agccca                                                   16
```

```
<210> SEQ ID NO 33
<211> LENGTH: 16
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(16)
<223> OTHER INFORMATION: D-Lys-modified

<400> SEQUENCE: 33
cagtttggcc agccca                                                 16

<210> SEQ ID NO 34
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 34
tttggccagc ccaaaatctg t                                           21

<210> SEQ ID NO 35
<211> LENGTH: 18
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(18)
<223> OTHER INFORMATION: D-Lys-modified

<400> SEQUENCE: 35
ggccagccca aaatctgt                                               18

<210> SEQ ID NO 36
<211> LENGTH: 15
<212> TYPE: DNA
<213> ORGANISM: artificial
<220> FEATURE:
<223> OTHER INFORMATION: Synthetic

<400> SEQUENCE: 36
acccagcagt ttggc                                                  15

<210> SEQ ID NO 37
<211> LENGTH: 15
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: D-Lys-modified

<400> SEQUENCE: 37
acccagcagt ttggc                                                  15

<210> SEQ ID NO 38
```

```
<211> LENGTH: 13
<212> TYPE: DNA
<213> ORGANISM: artificial
<220> FEATURE:
<223> OTHER INFORMATION: Synthetic

<400> SEQUENCE: 38
gctgcgtgat gag                                                        13

<210> SEQ ID NO 39
<211> LENGTH: 12
<212> TYPE: DNA
<213> ORGANISM: artificial
<220> FEATURE:
<223> OTHER INFORMATION: Synthetic

<400> SEQUENCE: 39
gctgcgtgat ga                                                         12

<210> SEQ ID NO 40
<211> LENGTH: 20
<212> TYPE: DNA
<213> ORGANISM: artificial
<220> FEATURE:
<223> OTHER INFORMATION: Synthetic

<400> SEQUENCE: 40
agctcatcac gcagctcatg                                                 20

<210> SEQ ID NO 41
<211> LENGTH: 22
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(22)
<223> OTHER INFORMATION: D-Lys-modified

<400> SEQUENCE: 41
cagctcatca cgcagctcat gc                                              22

<210> SEQ ID NO 42
<211> LENGTH: 22
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(22)
<223> OTHER INFORMATION: D-Lys-modified

<400> SEQUENCE: 42
tcatcacgca gctcatgccc tt                                              22

<210> SEQ ID NO 43
<211> LENGTH: 18
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(18)
<223> OTHER INFORMATION: D-Lys-modified

<400> SEQUENCE: 43
```
ctcatcacgc agctcatg                                              18

<210> SEQ ID NO 44
<211> LENGTH: 14
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(14)
<223> OTHER INFORMATION: D-Lys-modified

<400> SEQUENCE: 44
tgagctgcgt gatg                                                  14

<210> SEQ ID NO 45
<211> LENGTH: 20
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(20)
<223> OTHER INFORMATION: D-Lys-modified

<400> SEQUENCE: 45
tccacgctgg ccatcacgta                                            20

<210> SEQ ID NO 46
<211> LENGTH: 20
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(20)
<223> OTHER INFORMATION: D-Lys-modified

<400> SEQUENCE: 46
tccacgctgg ccatcacgta                                            20

<210> SEQ ID NO 47
<211> LENGTH: 14
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(14)
<223> OTHER INFORMATION: D-Lys-modified

<400> SEQUENCE: 47 tggggttgt ccac                                                   14

<210> SEQ ID NO 48
<211> LENGTH: 15
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: D-Lys-modified

<400> SEQUENCE: 48
gcacacgtgg gggtt                                                    15

<210> SEQ ID NO 49
<211> LENGTH: 17
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(17)
<223> OTHER INFORMATION: D-Lys-modified

<400> SEQUENCE: 49
acaaccccca cgtgtgc                                                  17

<210> SEQ ID NO 50
<211> LENGTH: 16
<212> TYPE: DNA
<213> ORGANISM: artificial
<220> FEATURE:
<223> OTHER INFORMATION: Synthetic

<400> SEQUENCE: 50
ctgagccagg agaaac                                                   16

<210> SEQ ID NO 51
<211> LENGTH: 17
<212> TYPE: DNA
<213> ORGANISM: artificial
<220> FEATURE:
<223> OTHER INFORMATION: Synthetic

<400> SEQUENCE: 51
gtaaactgag ccaggag                                                  17

<210> SEQ ID NO 52
<211> LENGTH: 20
<212> TYPE: DNA
<213> ORGANISM: artificial
<220> FEATURE:
<223> OTHER INFORMATION: Synthetic

<400> SEQUENCE: 52
atggcactag taaactgagc                                               20

<210> SEQ ID NO 53
<211> LENGTH: 21
<212> TYPE: DNA
<213> ORGANISM: artificial
<220> FEATURE:
<223> OTHER INFORMATION: Synthetic

<400> SEQUENCE: 53
atccatataa ctgaaagcca a                                             21

<210> SEQ ID NO 54
<211> LENGTH: 23
<212> TYPE: DNA
<213> ORGANISM: artificial
<220> FEATURE:
<223> OTHER INFORMATION: Synthetic

<400> SEQUENCE: 54
accacatcat ccatataact gaa                                           23

```
<210> SEQ ID NO 55
<211> LENGTH: 17
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(17)
<223> OTHER INFORMATION: D-Lys-modified

<400> SEQUENCE: 55
ttgcccacac cgccggc                                                  17

<210> SEQ ID NO 56
<211> LENGTH: 16
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(16)
<223> OTHER INFORMATION: D-Lys-modified

<400> SEQUENCE: 56
tcttgcccac accgcc                                                   16

<210> SEQ ID NO 57
<211> LENGTH: 17
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(17)
<223> OTHER INFORMATION: D-Lys-modified

<400> SEQUENCE: 57
tactcctcct ggccggc                                                  17

<210> SEQ ID NO 58
<211> LENGTH: 23
<212> TYPE: DNA
<213> ORGANISM: artificial
<220> FEATURE:
<223> OTHER INFORMATION: Synthetic

<400> SEQUENCE: 58
cgtctccaca gacacatact cca                                           23

<210> SEQ ID NO 59
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 59
cgtctccaca gacacatact cca                                           23

<210> SEQ ID NO 60
```

```
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 60
gcctacgcca ccagctccaa c                                              21

<210> SEQ ID NO 61
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 61
gcctacgcca ccagctccaa c                                              21

<210> SEQ ID NO 62
<211> LENGTH: 24
<212> TYPE: DNA
<213> ORGANISM: artificial
<220> FEATURE:
<223> OTHER INFORMATION: Synthetic

<400> SEQUENCE: 62
ctacgccacc agctccaact acca                                           24

<210> SEQ ID NO 63
<211> LENGTH: 24
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(24)
<223> OTHER INFORMATION: D-Lys-modified

<400> SEQUENCE: 63
ctacgccacc agctccaact acca                                           24

<210> SEQ ID NO 64
<211> LENGTH: 23
<212> TYPE: DNA
<213> ORGANISM: artificial
<220> FEATURE:
<223> OTHER INFORMATION: Synthetic

<400> SEQUENCE: 64
tcttgcctac gccaccagct cca                                            23

<210> SEQ ID NO 65
<211> LENGTH: 23
<212> TYPE: DNA
<213> ORGANISM: artificial
<220> FEATURE:
<223> OTHER INFORMATION: Synthetic

<400> SEQUENCE: 65
```

-continued tgtactcctc ttgacctgct gtg                                               23

<210> SEQ ID NO 66
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: 1modified_base
<222> LOCATION: (1)..(23)
<223> OTHER INFORMATION: D-Lys-modified

<400> SEQUENCE: 66
tgtactcctc ttgacctgct gtg                                               23

<210> SEQ ID NO 67
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: amino modified

<400> SEQUENCE: 67
ggcaaatcac atttatttcc tac                                               23

<210> SEQ ID NO 68
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 68
ggcaaatcac atttatttcc tac                                               23

<210> SEQ ID NO 69
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 69
tgtcttgtct ttgctgatgt ttc                                               23

<210> SEQ ID NO 70
<211> LENGTH: 23
<212> TYPE: DNA
<213> ORGANISM: artificial
<220> FEATURE:
<223> OTHER INFORMATION: Synthetic

<400> SEQUENCE: 70
tgtcttgtct ttgctgatgt ttc                                               23

<210> SEQ ID NO 71
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 71
tgtcttgtct ttgctgatgt ttc                                           23

<210> SEQ ID NO 72
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified
<220> FEATURE:
<221> NAME/KEY: modified_base
<222> LOCATION: (1)..(21)
<223> OTHER INFORMATION: Amino modified

<400> SEQUENCE: 72
ctcttgacct gctgtgtcga g                                             21

<210> SEQ ID NO 73
<211> LENGTH: 21
<212> TYPE: DNA
<213> ORGANISM: artificial
<220> FEATURE:
<223> OTHER INFORMATION: Synthetic

<400> SEQUENCE: 73
tcccaacacc acctgctcca a                                             21

<210> SEQ ID NO 74
<211> LENGTH: 25
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(25)
<223> OTHER INFORMATION: D-Lys-modified

<400> SEQUENCE: 74
caacaccacc tgctccaacc accac                                         25

<210> SEQ ID NO 75
<211> LENGTH: 23
<212> TYPE: DNA
<213> ORGANISM: artificial
<220> FEATURE:
<223> OTHER INFORMATION: Synthetic

<400> SEQUENCE: 75
cttttcccaa caccacctgc tcc                                           23

<210> SEQ ID NO 76
<211> LENGTH: 25

```
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(25)
<223> OTHER INFORMATION: D-Lys-modified

<400> SEQUENCE: 76
tgcgcttttc ccaacaccac ctgct                                        25

<210> SEQ ID NO 77
<211> LENGTH: 23
<212> TYPE: DNA
<213> ORGANISM: artificial
<220> FEATURE:
<223> OTHER INFORMATION: Synthetic

<400> SEQUENCE: 77
ggcactgtac tcttcttgtc cag                                          23

<210> SEQ ID NO 78
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 78
tctggtcttg gctgaggttt c                                            21

<210> SEQ ID NO 79
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: Amino modified

<400> SEQUENCE: 79
ggcaaatcac acttgtttcc cac                                          23

<210> SEQ ID NO 80
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: 1modified_base
<222> LOCATION: (1)..(23)
<223> OTHER INFORMATION: D-Lys-modified

<400> SEQUENCE: 80
ggcaaatcac acttgtttcc cac                                          23

<210> SEQ ID NO 81
<211> LENGTH: 25
<212> TYPE: DNA
<213> ORGANISM: artificial
<220> FEATURE:
```

<223> OTHER INFORMATION: Synthetic
<220> FEATURE:
<221> NAME/KEY: modified_base
<222> LOCATION: (1)..(25)
<223> OTHER INFORMATION: Amino modified

<400> SEQUENCE: 81
ttcttgtcca gctgtatcca gtatg                                              25

<210> SEQ ID NO 82
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 82
agatcctctc tctgaaatca c                                                  21

<210> SEQ ID NO 83
<211> LENGTH: 24
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(24)
<223> OTHER INFORMATION: D-Lys-modified

<400> SEQUENCE: 83
tctttctcct gctcagtgat ttca                                               24

<210> SEQ ID NO 84
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 84
aatgatgcac atcatggtgg ctg                                                23

<210> SEQ ID NO 85
<211> LENGTH: 23
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(23)
<223> OTHER INFORMATION: D-Lys-modified

<400> SEQUENCE: 85
ggcactgtac tcttcttgtc cag                                                23

<210> SEQ ID NO 86
<211> LENGTH: 26
<212> TYPE: DNA
<213> ORGANISM: artificial

<220> FEATURE:
<223> OTHER INFORMATION: Synthetic
<220> FEATURE:
<221> NAME/KEY: modified_base
<222> LOCATION: (1)..(26)
<223> OTHER INFORMATION: Amino modified

<400> SEQUENCE: 86
ttcatcaacc gcactctgtt tatctc                                        26

<210> SEQ ID NO 87
<211> LENGTH: 25
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(25)
<223> OTHER INFORMATION: Amino modified

<400> SEQUENCE: 87
tggcgacgac aatggaccca attat                                         25

<210> SEQ ID NO 88
<211> LENGTH: 30
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(30)
<223> OTHER INFORMATION: Amino modified

<400> SEQUENCE: 88
agatgtagtt agcaatcggt ccttgttgta                                    30

<210> SEQ ID NO 89
<211> LENGTH: 30
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(30)
<223> OTHER INFORMATION: Amino modified

<400> SEQUENCE: 89
gggtaattga ggtaacgtag gtatcaagat                                    30

<210> SEQ ID NO 90
<211> LENGTH: 27
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(27)
<223> OTHER INFORMATION: Amino modified

<400> SEQUENCE: 90
tactatcgac tgacatgagg cttgtgt                                       27

<210> SEQ ID NO 91
<211> LENGTH: 20
<212> TYPE: DNA

```
<213> ORGANISM: artificial
<220> FEATURE:
<223> OTHER INFORMATION: Synthetic
<220> FEATURE:
<221> NAME/KEY: modified_base
<222> LOCATION: (1)..(20)
<223> OTHER INFORMATION: D-Lys-modified

<400> SEQUENCE: 91
agtccgacga tctggaattc                                              20

<210> SEQ ID NO 92
<211> LENGTH: 19
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(19)
<223> OTHER INFORMATION: D-Lys-modified

<400> SEQUENCE: 92
actggagttc agacgtgtg                                               19

<210> SEQ ID NO 93
<211> LENGTH: 20
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(20)
<223> OTHER INFORMATION: D-Lys-modified

<400> SEQUENCE: 93
ctcttccgat cagatcggaa                                              20

<210> SEQ ID NO 94
<211> LENGTH: 21
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(21)
<223> OTHER INFORMATION: D-Lys-modified

<400> SEQUENCE: 94
ctcttccgat cagatcggaa g                                            21

<210> SEQ ID NO 95
<211> LENGTH: 15
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: D-Lys-modified

<400> SEQUENCE: 95
agcgctcccc gcacc                                                   15

<210> SEQ ID NO 96
<211> LENGTH: 15
```

```
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: D-Lys-modified

<400> SEQUENCE: 96
agcgctcccc gcacc                                                    15

<210> SEQ ID NO 97
<211> LENGTH: 14
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(14)
<223> OTHER INFORMATION: D-Lys-modified

<400> SEQUENCE: 97
ggggagcgct ctgt                                                     14

<210> SEQ ID NO 98
<211> LENGTH: 15
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(15)
<223> OTHER INFORMATION: D-Lys-modified

<400> SEQUENCE: 98
agcgctcccc gcacc                                                    15

<210> SEQ ID NO 99
<211> LENGTH: 20
<212> TYPE: DNA
<213> ORGANISM: artificial
<220> FEATURE:
<223> OTHER INFORMATION: Synthetic
<220> FEATURE:
<221> NAME/KEY: modified_base
<222> LOCATION: (1)..(20)
<223> OTHER INFORMATION: D-Lys-modified

<400> SEQUENCE: 99
tgcatacaca ctgcccgcct                                               20
```